US007083954B2

(12) United States Patent
Jakel et al.

(10) Patent No.: US 7,083,954 B2
(45) Date of Patent: *Aug. 1, 2006

(54) METHOD OF PRODUCING FERMENTATION-BASED PRODUCTS FROM CORN

(75) Inventors: Neal Torrey Jakel, Lake Zurich, IL (US); James F. Ulrich, Highwood, IL (US)

(73) Assignee: Renessen LLC, Deerfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/368,521

(22) Filed: Feb. 18, 2003

(65) Prior Publication Data
US 2003/0224496 A1 Dec. 4, 2003

Related U.S. Application Data

(63) Continuation-in-part of application No. 10/047,725, filed on Jan. 15, 2002, now Pat. No. 6,610,867, which is a continuation-in-part of application No. 09/927,836, filed on Aug. 10, 2001, now Pat. No. 6,648,930, and a continuation-in-part of application No. 09/637,843, filed on Aug. 10, 2000, which is a continuation-in-part of application No. 09/249,280, filed on Feb. 11, 1999, now Pat. No. 6,313,328.

(51) Int. Cl.
*C12P 7/64* (2006.01)
*C12P 7/12* (2006.01)
(52) U.S. Cl. ...................... 435/134; 435/161
(58) Field of Classification Search ................ 435/134, 435/161
See application file for complete search history.

(56) References Cited

U.S. PATENT DOCUMENTS

| 3,432,529 | A | 3/1969 | Demper |
| 3,519,431 | A | 7/1970 | Wayne |
| 3,786,078 | A | 1/1974 | Finley et al. |
| 3,909,288 | A | 9/1975 | Powell et al. |
| 3,939,281 | A | 2/1976 | Schwengers |
| 4,008,210 | A | 2/1977 | Steele et al. |
| 4,246,184 | A | 1/1981 | Pressick et al. |
| 4,277,411 | A | 7/1981 | Yahl |
| 4,310,468 | A | 1/1982 | Reiners |
| 4,341,713 | A | 7/1982 | Stolp et al. |
| 4,442,034 | A | 4/1984 | Suzuki et al. |
| 4,456,556 | A | 6/1984 | Grimsby |
| 4,456,557 | A | 6/1984 | Grimsby |
| 4,486,353 | A | 12/1984 | Matsuzaki et al. |
| 4,495,207 | A | 1/1985 | Christianson et al. |
| 4,594,260 | A | 6/1986 | Vaqueiro et al. |
| 5,035,910 | A | 7/1991 | Jones et al. |
| 5,085,808 | A | 2/1992 | Snyder et al. |
| 5,320,669 | A | 6/1994 | Lim et al. |
| 5,408,924 | A | 4/1995 | Arendt et al. |
| 5,525,746 | A | 6/1996 | Franke |
| 5,670,678 | A | 9/1997 | Rothbart |
| 5,675,065 | A | 10/1997 | Bergquist |
| 5,706,603 | A | 1/1998 | Bergquist et al. |
| 5,750,851 | A | 5/1998 | Geadelmann et al. |
| 5,851,572 | A | 12/1998 | Cook et al. |
| 5,908,940 | A | 6/1999 | Lane et al. |
| 6,703,227 | B1 | 3/2004 | Jakel et al. |
| 6,723,370 | B1 | 4/2004 | Ulrich et al. |
| 2003/0180897 | A1* | 9/2003 | Ulrich et al. ............... 435/134 |

FOREIGN PATENT DOCUMENTS

| EP | 0623100 B1 | 4/1997 |
| GB | 2269084 A | 2/1994 |
| GB | 2309150 A | 7/1997 |
| JP | 6032358 | 2/1994 |
| JP | 10195400 | 7/1998 |
| WO | WO 94/15483 A1 | 7/1994 |
| WO | WO 95/22598 A2 | 8/1995 |
| WO | WO 98/43473 A1 | 10/1998 |
| WO | WO 99/52376 A1 | 10/1999 |
| WO | WO 00/10404 | 3/2000 |
| WO | WO 00/47702 A1 | 8/2000 |
| WO | WO 01/55283 A1 | 8/2001 |
| WO | WO 02/13624 A1 | 2/2002 |
| WO | WO 02/14459 A2 | 2/2002 |

OTHER PUBLICATIONS

Liu et al., "Quick (seeking Fast) Development of High Oil Corn," Agriculture & Technology 20(1):59-60 (Feb. 2000). (English Translation with Chinese Original).
Aguilera et al., "Laboratory and Pilot Solvent Extraction of Extruded High-Oil Corn," *JAOCS*, 1986, 63(2): pp. 239-243, Texas A&M University, College Station, Texas, USA.
Bockisch, Michael, "Fats and Oils Handbook," 1993, pp. 344, 345 & 360-391, Hamburg, Germany.
Midwest Research Institute For The Office Of Air Quality And Planning And Standards, Emission Factor Documentation for AP-42, Section 9.11.1, "Vegetable Processing," Final Report, Nov. 1995, p. 2-12, Research Triangle Park, North Carolina, USA.
Watson, "Corn and Corn Improvement," *Marketing, Processing and Utilization*, 3rd Edition, 1988, No. 18 series Agronomy, pp. 917-918, Madison, Wisconsin, USA.

(Continued)

*Primary Examiner*—Deborah D. Carr
(74) *Attorney, Agent, or Firm*—Leydig, Voit & Mayer, Ltd.

(57) ABSTRACT

Corn oil and corn meal obtained from corn are included in useful products. A method for producing fermentation-based products comprises combining corn meal with water and an enzyme, and mixing the combination with a micro-organism capable of fermenting a carbon source to produce a fermentation-based product. The corn meal is produced by cracking whole corn, conditioning the whole corn and extracting the whole corn to produce corn meal without flaking the corn during processing. The corn grain process generally includes the steps of cracking corn grain having a total oil content of from about 3% by weight to about 30% by weight and extracting a corn oil from the cracked corn grain.

17 Claims, No Drawings

OTHER PUBLICATIONS

Watson et al., "Structure and Composition" *Corn: Corn Chemistry and Technology*, 1987, pp. 538-539, St. Paul, Minnesota, USA.

Blessin, "Carotenoids of Corn and Sorghum," *Cereal Chem.*, 59:236-242 (1962).

Blessin et al., "Carotenoids of Corn and Sorghum," *Cereal Chem.*, 40:582-586 (1963).

Grams et al., "Distribution of Tocopherols Within The Corn Kernel," *J. Amer. Oil Chemists Soc.*, 47:337-339 (1970).

Lambert, "High-Oil Corn Hybrids," *Specialty Corns*, pp. 123-145 (1994).

Paulis et al., "Selection of High-Lysine Corns with Varied Kernel Characteristics and Compositions of a Rapid Turbidimetric Assay for Zein," *J. Agr. Food Chem.*, 22:318-323.

AOCS Recommended Practice Ba 2b-82 (1997).
AOCS Recommended Practice Ba 4e-93 (1999).
AOCS Recommended Practice Ba 6-84 (1997).
AOCS Recommended Practice Ba 3-38 (1997).
AOCS Recommended Practice Ca 5a-40 (1997).
AOCS Official Method Ca 12-55 (1997).
AOCS Official Method Cc 13b-45 (2000).
Standard Analytical Methods of the Member Companies of the Corn Refiners Association, Inc., Standard Jun. 3, 1957 (1996).
XP-002199802, DuPont Quality Grains (1996).
S. H. Kaplan, "Modified Dry Milling Of Corn Grain," Research Disclosure Journal, 384(035):1-5 (1996).
European Search Report for EP00954043, May 4, 2005.

* cited by examiner

METHOD OF PRODUCING FERMENTATION-BASED PRODUCTS FROM CORN

The present application is a continuation-in-part of copending U.S. patent application Ser. No. 10/047,725, filed Jan. 15, 2002 now U.S. Pat. No. 6,610,867, which is a continuation-in-part of U.S. patent application Ser. No. 09/927,836, filed Aug. 10, 2001 now U.S. Pat. No. 6,648,930, which is a continuation-in-part of co-pending U.S. patent application Ser. No. 09/637,843, filed Aug. 10, 2000, the entire disclosures of which are hereby incorporated by reference.

FIELD OF THE INVENTION

The present invention relates to a method for extracting oil from whole corn with a total oil content of about 3% by weight to about 30% by weight and the products that are derived from the extracted corn.

BACKGROUND OF THE INVENTION

Corn, *Zea mays L.*, is grown for many reasons including its use in food and industrial applications. Corn oil and corn meal are two of many useful products derived from corn.

Commercial processing plants utilizing conventional methods for extracting corn oil from normal yellow #2 corn separate the corn seed into its component parts, e.g., endosperm, germ, tipcap, and pericarp, and then extract corn oil from the corn germ fraction. Corn germ produced by wet or dry milling is processed either by pressing the germ to remove the oil or by flaking the germ and extracting the oil with a solvent. In both processes, because the germ was separated from the remainder of the kernel, many or all of the valuable components of the endosperm fraction are absent from the oil.

A corn-based feed product known as hominy feed is obtained from the dry milling process and is a mixture of corn bran, corn germ, and endosperm, and has a minimum of about 3% by weight oil. Several steps, including cracking, grinding, sieving, and blending are required to manufacture hominy feed and the resulting particle size of hominy feed is small relative to meal made by the extraction method described herein.

Industry and health advocates are continually in search of more nutritious products derived from corn, since products derived from normal yellow #2 corn lack some desired nutritional components. Thus, there exists a need for improved products derived from corn oil and corn meal. Additionally, there exists a need for new processes for processing the corn.

BRIEF SUMMARY OF THE INVENTION

Finished products containing corn oil and/or corn meal obtained from corn processed by conventional wet and dry milling include, for example, cooking oil, animal feed, paper and paper products, numerous food products such as salad dressings, extruded and/or puffed snack foods, products containing corn sweeteners, cereals, chips, puddings, candies, and breads.

One aspect of the invention involves an optional process applicable to corn having an oil content from about 3% by weight to about 30% by weight (e.g., about 3% to about 20% by weight; about 3% to about 15% by weight; about 3% to about 10% by weight; about 3% to about 8% by weight; about 3% to about 6% by weight; about 6% to about 12% by weight). The process may include tempering whole corn to a specific moisture and temperature level followed by cracking the grain. The process breaks the whole kernel corn into smaller pieces. The cracked corn is then conditioned before being subjected to an extraction process. The conditioning step may include applying steam or indirect heat. The cracked corn is heated to a minimum of about 20° C. and a maximum of about 110° C. prior to the extraction process. Conditioning makes the corn more pliable, helping to release the oil bodies during the extraction step. After conditioning, the cracked corn is fed to the extractor for, for example, solvent extraction. The extraction process can be that of existing methods for multiseed and soybean oil extraction operations. In one embodiment of the present invention, the process of the present invention reduces the number of steps in processing corn, e.g., by eliminating the flaking step. Further, the process of the present invention reduces the amount of "fines" by eliminating the flaking step.

One aspect of the invention provides a nutritious animal feed comprising the corn meal remaining after extraction of oil from corn having an oil content of about 3% by weight to about 30% by weight (e.g., about 3% to about 20% by weight; about 3% to about 15% by weight; about 3% to about 10% by weight; about 3% to about 8% by weight; about 3% to about 6% by weight; about 6% to about 12% by weight). The animal feed can comprise other nutritious products such as vitamins, minerals, seed-derived meal, meat and bone meal, salt, amino acids, feather meal, and many others used in the art of feed supplementation. The animal feed composition can be tailored for particular uses such as for poultry feed, swine feed, cattle feed, equine feed, aquaculture feed, pet food and can be tailored to animal growth phases. Particular embodiments of the animal feed include growing broiler feed, swine finishing feed, and poultry layer finishing feed. Feed products can be made with the extracted corn meal that will have a higher relative percentage of protein and similar relative percentage of oil than similar products made with corn produced by conventional wet or dry milling processes.

Some embodiments of the invention include those wherein: 1) the extracted corn meal has a fiber content of about 3%, a starch content of about 65%, and a protein content of about 10%, at a moisture content of about 10%; 2) the corn grain has a total oil content of between at least about 3% by weight and about 30% by weight; 3) the corn grain has been subjected to an oil extraction process such as solvent extraction, hydraulic pressing, or expeller pressing, aqueous and enzyme extraction; 4) the corn grain has a total protein content of at least about 7% by weight, at least about 9% by weight, at least about 11% by weight, or from about 7% by weight to about 20% by weight; 5) the corn grain has a total lysine content of at least about 0.15% by weight, at least about 0.5% by weight, or from about 0.15% by weight to about 2.0% by weight; and/or 6) the corn grain has a total tryptophan content of at least about 0.03% by weight, at least about 0.20% by weight, or from about 0.03% by weight to about 2.0% by weight.

In one embodiment, the method of processing corn includes a cracking step before conditioning the corn. Cracking the corn breaks the cell structure of the corn and enhances the extractability of the oil. In addition, cracking the corn increases the available surface area for extraction. The extraction step exposes the cracked corn grain to solvent-based oil extractions. Solvents used to extract miscible or soluble substances from the cracked grain include hexane, n-hexane, isopropyl alcohol, ethanol and supercritical carbon dioxide. The method of processing corn is preferably accomplished without flaking the corn.

A preferred embodiment provides a method of obtaining corn oil and solvent extracted corn meal (SEC) from normal yellow #2 corn and from high oil corn. The method provides steps of: 1) optionally tempering the corn; 2) cracking the tempered corn in a manner to reduce the production of "fines"; 3) conditioning the cracked corn; 4) extracting the cracked corn; and 5) removing the solvent from both the corn oil and solvent extracted corn meal. The method provides a greater overall content of corn oil in the corn meal as compared to meal produced by the method set forth in U.S. Pat. No. 6,313,328 (incorporated herein by reference) and concentrates the proteins in the meal. Moreover, solvent extractable pigments can be removed from the SEC.

Another aspect of the invention provides a corn oil-based product comprising corn oil obtained by extraction of at least the endosperm and germ of the corn. The corn oil-based product can comprise other components such as vinegar, spices, vitamins, salt, hydrogen (for forming hydrogenated products), and water. The corn oil used in the products of the invention will generally contain a higher proportion of β-carotene or tocotrienol than similar products made with corn oil extracted from corn employing conventional methods. The corn oil, used in the products of the invention, is generally produced by exposing the entire corn grain or the cracked corn grain to extraction without separation of the germ from the endosperm. Therefore, the solvent-extractable nutrients present in the endosperm are extracted into the corn oil that has been extracted from the germ and endosperm. Products that can be made with the oil prepared as described herein include, but are not limited to, salad dressings, cooking oils, margarines, spray-coated food or feed products, breads, crackers, snack foods, lubricants, and fuels.

Other embodiments of the invention include those wherein: 1) corn grain is cracked, conditioned and extracted with a solvent; 2) the corn grain has a total oil content of between about 3% by weight and about 30% by weight; 3) the corn oil is extracted by subjecting cracked corn grain to a solvent-based extraction process; 4) the solvents used to extract miscible or soluble substances from the cracked corn include all forms of commercially available hexanes, isopropyl alcohol, ethanol, supercritical carbon dioxide or mixtures thereof; 5) the extracted corn oil is provided as miscella; 6) the corn oil is refined by additional processing; and 7) the corn oil is extracted by subjecting cracked corn grain to hydraulic pressing and/or expeller pressing, aqueous and/or enzyme extraction processes.

A third aspect of the invention provides a method of using extracted corn meal in an animal feed ration comprising the step of: 1) providing an extracted corn meal prepared by cracking corn and extracting the cracked corn to remove a portion of the corn oil therefrom; and 2) including the extracted corn meal in an animal feed ration.

A fourth aspect of the invention provides a method of using an extracted corn oil in a food product comprising the steps of: 1) providing an extracted corn oil obtained by cracking corn and extracting the cracked corn to remove a portion of the corn oil therefrom and form the extracted corn oil; and 2) including the extracted corn oil in a food product.

A fifth aspect of the invention provides a method of using extracted corn oil as a feedstock in an oil refining process. The method comprises the steps of: 1) providing an extracted crude corn oil obtained by at least cracking corn and extracting the cracked corn to remove a portion of the corn oil therefrom and form the extracted crude corn oil; and 2) including the extracted crude corn oil in a raw material stream of an oil refining process.

A sixth aspect of the invention provides various methods of forming extracted blended meals. A first embodiment of this aspect of the invention provides a method of forming an extracted blended meal comprising an extracted meal obtained from corn and one or more other oilseed meals, the method comprising the step of: 1) combining corn grain and one or more other oilseed grains to form a grain mixture; and 2) subjecting the grain mixture to cracking and an extraction process to remove oil therefrom and form the extracted blended meal. A second embodiment provides a method comprising the steps of: 1) combining a cracked and conditioned corn with another cracked and conditioned oilseed to form a conditioned mixture; and 2) subjecting the cracked mixture to an extraction process to remove oil therefrom and form the extracted blended meal. A third embodiment provides a method comprising the steps of: 1) combining a cracked and conditioned corn with a cracked and conditioned other oilseed to form a cracked mixture; and 2) subjecting the cracked mixture to an extraction process to remove oil therefrom and form the extracted blended meal. A fourth embodiment provides a method comprising the step of combining an extracted corn meal with one or more extracted other oilseed meals to form a blended meal, wherein the extracted corn meal has been obtained by cracking and extracting corn to form the extracted corn meal. A fifth embodiment provides a method comprising the step of combining an extracted corn meal with one or more other extracted oilseed meals to form a blended meal, wherein the extracted corn meal has been obtained by cracking and extracting corn to form the extracted corn meal and the other oilseed has been cracked, conditioned, flaked and extracted to form the extracted oilseed meal. A sixth embodiment provides a blended extracted meal product prepared according to any one of the above-described methods.

A seventh aspect of the invention provides a method of using extracted corn oil as an ingredient in cosmetic applications. The method comprises the steps of: 1) providing an extracted crude corn oil obtained by cracking corn and extracting the cracked corn to remove a portion of the corn oil therefrom and form the extracted crude corn oil; and 2) including the extracted crude corn oil in a cosmetic product. These types of cosmetics include but are not limited to lipstick and eyeliner.

Another aspect of the invention provides the use of a corn meal in an animal feed or human food, wherein the corn meal is obtained after extraction of corn oil from whole kernels of corn.

Other aspects of the invention provide corn oil-containing and/or corn meal-containing products made by the processes described herein.

In addition, the present invention provides a method of producing fermentation-based products from corn meal. Such fermentation-based products include ethanol and citric acid. The method comprises 1) combining an enzyme, water, and a corn meal obtained by cracking the corn, conditioning the corn, and extracting the corn to produce corn meal and corn oil, wherein the corn is not flaked during processing; 2) incubating the combination; and 3) mixing the combination with a micro-organism capable of fermenting a carbon source to produce fermentation-based products. The enzyme is any enzyme suitable for fermentation of corn, including an amylase, a protease, a cellulase, an esterase and a liginase. The grain of the whole corn typically has a total oil content of from about 3% by weight to about 30% by weight (e.g., about 3% to about 20% by weight; about 3% to about 15% by weight; about 3% to about 10% by weight; about 3% to about 8% by weight; about 3% to about 6% by weight; about 6% to about 12% by weight). The whole corn can be optionally tempered and/or conditioned in order to obtain the corn meal.

Unless otherwise defined, all technical and scientific terms and abbreviations used herein have the same meaning as commonly understood by one of ordinary skill in the art to which this invention pertains. Although methods and materials similar or equivalent to those described herein can be used in the practice of the present invention, suitable methods and materials are described below without intending that any such methods and materials limit the invention described herein. Additional features and advantages of the invention will be apparent from the following description of illustrative embodiments of the invention and from the claims.

DETAILED DESCRIPTION OF THE INVENTION

It has been discovered that corn oil can be rapidly and efficiently extracted on a commercial-scale from corn grain having an oil content of from about 3% by weight to about 30% by weight by cracking the corn, conditioning the corn and extracting a corn oil, preferably without flaking the corn. Suitable extracting equipment and methods may include conventional methods used for extracting oil from soybean flakes and other similar oilseed types.

Corn seed or "grain" harvested from any of several different types of corn plants is useful in the invention. These types of corn plants are, for example, yellow #2 corn, as well as hybrids, inbreds, transgenic plants, genetically modified plants or a specific population of plants. Enhanced extracted meals can be made by subjecting corn to the extraction process described herein. Useful corn grain types include, for example, flint corn, popcorn, flour corn, dent corn, white corn, and sweet corn. The corn grain can be in a form including whole corn or cracked corn.

As used herein, the terms "whole kernel" or "whole corn" mean a kernel that has not been purposefully separated into its constituent parts, e.g. the hull, endosperm, tipcap, pericarp, and germ. The whole corn may or may not have been ground, crushed, cracked, or abraded. Purposeful separation of one corn constituent from another does not include random separation that may occur during storage, handling, transport, crushing, and cracking, grinding or abrading. A purposeful separation of the constituent part is one wherein at least 50% of one constituent, e.g., germ, has been separated from the remaining constituents.

As used herein, the term "cracking" means any process capable of reducing the starting grain particle size by at least 50%. Equipment to practice such processes include, but are not limited to, the following devices and classes of devices: roller mills, disk mills, pin mills, Urshel cutters, Fitz mills, hammer mills, grinders/granulators, and other impact or acceleration devices. Single or multiple passes of the device may be used to achieve the desired particle size. The rotational energy from roller mills utilize single or multiple strands of corrugated or uncorrugated cylinder pairs. Disk mills utilize rotating disks with teeth to grind grain. Pin mills, Urshel cutters, Fitz mills, hammer mills, grinders/granulators, and other impact devices utilize the energy from rotating pins, knives, or hammers. Other size reduction devices can act upon grain with a reciprocating rather than rotational action. Acceleration devices act upon grain by accelerating it into a solid object, thereby shattering the grain.

As used herein, the term "high oil corn" refers to corn grain comprising at least about 6% by weight or greater, preferably at least about 7% by weight or greater, and preferably at least about 8% by weight or greater oil. A high oil corn has an elevated level of oil as compared to yellow #2 corn, which generally has an oil content of from about 3% by weight to about 6% by weight. Although the oil content can be determined at any moisture content, it is acceptable to normalize the oil content to a moisture content of about 15.5%. High oil corn useful in making the oil and meal described herein are available from Monsanto Corporation (St. Louis, Mo.) or Pfister Hybrid Corn Co. (El Paso, Ill.). Other suitable high oil corn includes the corn populations known as Illinois High Oil (IHO) and Alexander High Oil (Alexo), samples of which are available from the University of Illinois Maize Genetics Cooperative—Stock Center (Urbana, Ill.).

The oil content of grain, including the fat content of a meal extracted from the grain, can be determined using American Oil and Chemical Society Official Method, $5^{th}$ edition, March 1998, ("AOCS method Ba 3-38"). AOCS method Ba 3-38 quantifies substances that are extracted by petroleum ether under conditions of the test. The oil content or concentration is the weight percentage of the oil with respect to the total weight of the seed sample. Oil content may be normalized and reported at any desired moisture basis.

Other suitable methods for identifying the levels of oil in corn grain are described herein. According to one method, corn ears are selected using a near infrared (NIR) oil detector to select corn ears. Likewise, an NIR detector can also be used to select individual corn kernels. Generally, corn seed producing corn plants that yield grain having elevated total oil concentrations is planted and harvested using known farming methods. Methods for developing corn inbreds, hybrids, transgenic species and populations that generate corn plants producing grain having elevated oil concentrations are known and described in Lambert (Specialty Corn, CRC Press Inc., Boca Raton, Fla., pp. 123–145 (1994). One of the suitable corns used as a raw material for preparing the corn oil and corn meal used in the invention has a nutrient profile as shown in Table 1. Amounts are expressed on an "as is" or "as fed" moisture level. Protein, oil, and starch levels can vary in a number of possible combinations in the corn used as a raw material for meal and oil used in the invention. Acceptable amounts of moisture, oil, protein, starch, lysine, and tryptophan are illustrated in Table 1. However, additional combinations, such as 12% by weight protein and 12% by weight oil, not shown as indicated amounts in the Table are within the scope and range of corn grain to be used to produce oil and meal used in the invention.

TABLE 1

| Component | Sample 1 (% by weight) | Sample 2 (% by weight) | Sample 3 (% by weight) | Sample 4 (% by weight) | General Amount (% by weight) |
|---|---|---|---|---|---|
| Moisture | 14 | 14 | 14 | 14 | 5–45 |
| Oil | 8 | 12 | 20 | 3.5 | 3–30 |
| Protein | 9 | 9 | 17 | 7.5 | 5–20 |
| Starch | 61 | 54 | 41 | 67 | 35–80 |
| Lysine | 0.35 | 0.50 | 1.0 | 0.22 | 0.15–2.0 |
| Tryptophan | 0.088 | 0.11 | 0.15 | 0.07 | 0.03–2.0 |

Another suitable high oil corn used as a raw material for preparing the corn oil and corn meal used in the invention has a nutrient profile as shown in Table 2. Amounts are expressed on an "as is" or "as fed" moisture level. The amounts shown in Table 2 are exemplary for a corn grain having 12% by weight oil and 9% by weight protein.

TABLE 2

| Component | Sample (% by weight) | General Amount (% by weight) |
| --- | --- | --- |
| Moisture | 14 | 5–45 |
| Oil | 12 | 3–30 |
| Protein | 9 | 5–20 |
| Starch | 60 | 35–80 |
| Fiber | 3 | 1–5 |
| Ash | 1.18 | 0.59–4.72 |
| Lysine | 0.33 | 0.15–2.0 |
| Tryptophan | 0.09 | 0.03–2.0 |
| Methionine | 0.25 | 0.13–1.00 |
| Total Sulfur Amino Acids | 0.46 | 0.23–1.84 |
| Valine | 0.45 | 0.23–1.80 |
| Isoleucine | 0.34 | 0.17–1.36 |
| Arginine | 0.45 | 0.23–1.80 |
| Threonine | 0.34 | 0.17–1.36 |
| Leucine | 1.03 | 0.52–4.12 |
| Histidine | 0.27 | 0.14–1.08 |
| Phenylalanine | 0.44 | 0.22–1.76 |
| Alanine | 0.70 | 0.35–2.80 |
| Aspartic | 0.74 | 0.37–2.96 |
| Cysteine | 0.22 | 0.11–0.88 |
| Glutamic | 1.9 | 0.95–7.6 |
| Glycine | 0.46 | 0.23–1.84 |
| Proline | 0.86 | 0.43–3.44 |
| Tyrosine | 0.06 | 0.03–0.54 |
| Serine | 0.46 | 0.23–1.84 |

Table 3 shows amino acid levels (based on a corn grain moisture content of about 10%) of two high oil corn grain samples and yellow #2 corn. The oil and protein levels of high oil corn sample 1 (HOC 1) were 13.3% by weight and 10.7% by weight respectively, expressed on a dry matter basis. The oil and protein levels of high oil corn sample 2 (HOC 2) were 13.0% by weight and 11.2% by weight respectively, expressed on a dry matter basis. For comparison, yellow #2 corn has about 4.2% by weight oil and about 9.2% by weight protein on a dry matter basis.

TABLE 3

| Amino Acid | HOC 1 (%) | HOC 2 (%) | Yellow Corn (%) |
| --- | --- | --- | --- |
| Aspartic Acid | 0.71 | 0.68 | 0.48 |
| Threonine | 0.33 | 0.30 | 0.19 |
| Serine | 0.37 | 0.27 | 0.19 |
| Glutamic Acid | 1.84 | 1.79 | 1.16 |
| Proline | 0.83 | 0.78 | 0.52 |
| Glycine | 0.40 | 0.42 | 0.24 |
| Alanine | 0.77 | 0.74 | 0.47 |
| Valine | 0.51 | 0.52 | 0.33 |
| Cystine | 0.21 | 0.23 | 0.16 |
| Methionine | 0.46 | 0.47 | 0.39 |
| Isoleucine | 0.30 | 0.30 | 0.20 |
| Leucine | 1.19 | 1.08 | 0.74 |
| Tyrosine | 0.11 | 0.11 | 0.06 |
| Phenylalanine | 0.52 | 0.48 | 0.32 |
| Tryptophan | 0.06 | 0.07 | 0.05 |
| Lysine | 0.34 | 0.38 | 0.21 |
| Histidine | 0.29 | 0.29 | 0.18 |
| Arginine | 0.45 | 0.48 | 0.28 |

Corn is generally subjected to an extraction process as described herein to provide the enhanced corn oil and corn meal to be included in the finished products of the invention. As used herein, the term "finished product" or "product" refers to an article or manufacture made by combining the corn oil and/or corn meal of the invention with a variety of other ingredients. The specific ingredients included in a product will be determined according to the ultimate use of the product. Exemplary products include animal feed, raw material for chemical modification, biodegradable materials, blended food product, edible oil, cooking oil, lubricant, biodiesel, snack food, cosmetics, and fermentation process raw material. Products incorporating the meal described herein also include complete or partially complete swine, poultry, and cattle feeds, pet foods, and human food products such as extruded snack foods, breads, as a food binding agent, aquaculture feeds, fermentable mixtures, food supplements, sport drinks, nutritional food bars, multi-vitamin supplements, diet drinks, and cereal foods. Products incorporating the starch described herein include, e.g., cardboard, paper products, and industrial materials.

For example, starting with a single corn type, more than one corn meal type can be made to meet certain nutritional requirements. The significance of this flexibility relates to the nutrient density within feed products and to dietary requirements of animals. One significant advantage of the use of this type of corn and extraction process is that an extracted corn meal can be made to have a specific oil level depending on the extent of oil extraction and/or the degree of cracking. Once the oil is removed from the flakes, the remaining corn meal has a nutrient density for protein, amino acids, and other nutrients not removed by the process, greater or different than normal corn grain and greater than that of the starting corn, e.g., 12% by weight oil, 9% by weight protein.

According to one extraction process used in preparing the corn oil and corn meal as described herein, whole grain corn is cracked, and then conditioned and extracted, preferably without flaking the corn. In avoiding flaking, the processor achieves a time savings while avoiding significant energy and processing costs. Whole grain corn is optionally tempered before the extraction process. As used herein, the term "tempering" is used interchangeably with the terms "heat soaking" or "steaming" and is a means to uniformly distribute the added moisture through the entire corn kernel. Any tempering method known in the art is acceptable. In general, the corn is steeped in an appropriate amount of water for any suitable length of time, such as at least 20 minutes, preferably at least 4 hours, preferably at least 6 hours, more preferably at least 12 hours, or most preferably at least 24 hours. After the corn is steeped for the desired length of time, its moisture content is retested. The corn may be stored for short periods of time, but is preferably processed within 24 hours and most preferably processed immediately.

In a preferred embodiment, the whole corn is cracked after tempering yet before conditioning. Tempering is an optional step if the moisture level of the corn is less than about 12%. Tempering reduces fines production during cracking. Cracking typically involves, at a minimum, one set of rollers spinning in opposite directions. The rollers typically are constructed of angled corrugated steel. The corrugations help rip the grain apart into several smaller pieces. The gap between the rollers can be adjusted to produce a wide range of cracked particle sizes. The corrugation on the rollers can have a variety of styles with the most commonly used style being the spiral cut modified Dawson. Other styles include LePage, and standard Dawson. See, for example, Heimann, Roskamp, Cracking Mill Performance and Developments (1999), 1–8 and Feed Manufacturing Technology Handbook, American Feed Industry Association, 4$^{th}$ Ed. A "cracked" corn is a corn that has undergone the above-described cracking process. The cracked corn may have a final thickness of from about 0.1 mm to about 1.0 mm, although other thicknesses may also be used. Preferably, cracked corn of a thickness that will pass through #6 mesh (3.36 mm) to #10 mesh (2.00 mm) sieve screens results from the cracking process. In accordance with this invention, it is contemplated that the cracked corn referred to in this paragraph is processed without flaking the corn. However, it is also contemplated that cracked corn of the above thickness (from about 0.1 mm to about 1.0 mm) can be processed regardless of whether the corn is flaked.

The corn may be conditioned using methods known to those of ordinary skill in the art and/or methods described herein. As used herein, the term "conditioning" refers to a process by which the cracked corn is heated prior to extraction to improve the extraction efficiency. Conditioning may include the addition of steam (saturated and/or non-saturated steam) and/or water to the corn. One method of conditioning the cracked grain is by the use of a rotary conditioner. The temperature ranges between about 60° C. and about 95° C. and the moisture can be increased up to about an additional 10%.

After the corn is cracked and/or conditioned, the cracked corn is subjected to an extraction process to extract oil to form an extracted corn meal (ECM). Corn oil is extracted from cracked grain by one or more extraction steps using any extraction method. Generally, substantially, or about all of the oil is extracted in a single extraction process. Useful extraction methods include solvent extraction, continuous solvent extraction, hydraulic pressing, expeller pressing, aqueous and/or enzyme extraction. Useful solvents for solvent extraction include, for example, all forms of commercially available pentane, hexanes, isopropyl alcohol, ethanol, supercritical carbon dioxide, combinations thereof, and other similar solvents. For example, corn oil can be extracted from cracked grain using a hexane-based solvent extractor. Solvent extractors can include both percolation and immersion type extractors. In a preferred embodiment, a continuous solvent extraction process allows the cracked corn to remain in contact with the solvent for at least 10 minutes, preferably at least 30 minutes, more preferably at least 60 minutes, and most preferably at least 90 minutes.

Materials removed from solvent-based extractors include wet cracks and miscella. A miscella is a mixture of extracted oil and solvent. The wet cracks are the materials that remain after some or all of the solvent-soluble material has been extracted. Wet cracks also contain a quantity of solvent. Solvent is reclaimed from both the miscella and wet cracks using methods such as rising film evaporation, or drying, and raising the temperature using equipment such as flash tanks and/or de-solventiser/toasters. For example, heat is applied to the wet cracks or miscella under atmospheric pressure, under elevated pressure, or under vacuum to evaporate the solvent. The evaporated solvent is then condensed in a separate recovery system, and optionally dewatered and recycled to the extractor.

Desolventized miscella is commonly termed crude oil, which can be stored and/or undergo further processing. Crude oil can be refined to produce a final oil product. Methods for refining crude oil to obtain a final oil are known to those of ordinary skill in the art. Hui (1996) provides a thorough review of oils and oilseeds (Bailey's Industrial Oil and Fat Products, Fifth Ed., Vol. 2, Wiley and Sons, Inc., New York, 1996). Chapter three of Hui (pp. 125–158), the disclosure of which is hereby incorporated by reference, specifically describes corn oil composition and processing methods. Crude oil isolated using the cracking methods described herein is of a high quality but can be further purified as needed using conventional oil refining methods.

In a preferred embodiment, the invention relates to a method of reducing the generation of lighter particles, such as fines. Fines are produced throughout the crushing and extracting processes from various sources. The cracking step is a significant generator of fines. Other sources of fines generation include the physical handling devices such as conveyors, as well as the conditioner, and aspiration systems most commonly used in an oilseed extraction plant.

Fines, if in amounts greater than 30% of the total amount of material fed to the extractor, measured as capable of passing through a #18 US Sieve (particle size less than 1 mm), can reduce solvent flow leading to lower oil extraction efficiency. Increased fines fed to an extractor can lead to an increase in solvent carry over from the extractor to the desolventizer. Moisture of the incoming cracked material to the extractor is important to proper extraction operation. Cracked corn with a moisture level above 15% can inhibit the extraction process due to the interaction of the solvent and the water.

In one embodiment of the present invention, a double cracking roller system is found to provide the combination of preferred particle size distribution while minimizing fines generation.

In a preferred embodiment, the present invention relates to a method of recovering lighter particles, such as fines, during the processing of whole kernel corn. As used herein, the term "fines" means any particle of the corn process that passes through a #18 sieve having a 1.00 mm opening as defined in ASTM E-11 specifications. The recovery of the particles may occur before, after, or during any step in the process, such as during the cracking step. In general, fines are recovered by passing a current of gas (e.g., air, nitrogen, argon) over the corn at a suitable velocity and direction such that smaller and lighter particles are carried away in the stream, leaving behind larger and heavier particles.

Alternatively, lighter particles can be separated from heavier particles using a liquid spray (e.g., water, process water, or oil). The liquid is applied broadly enough so as to physically eliminate the lighter, airborne particles. The liquid spray can include components that add value to the end product, such as vitamins, minerals, enzymes, and combinations thereof. In addition, the liquid spray can further comprise a caustic liquid.

Regardless of the separation method, these fine particles can be captured or recovered by any method known in the art such as using a baghouse. Preferably, the recovered lighter particles can be reintroduced into starch-containing product streams for the recovery of starch. Additionally the fines may be sold as an animal feed.

Corn endosperm includes some valuable components such as carotenoids, lutein, and zeaxanthin. Carotenoids in grains are classified into two general groups, the carotenes and the xanthophylls. The carotenes are important because they are vitamin A precursors. Blessin et al. (*Cereal Chemistry*, 40, 582–586(1963)) found that over 90% of the carotenoids, of which beta-carotene is predominant, are located in the endosperm of yellow #2 corn and less than 5% are located in the germ. Vitamin A is derived primarily from beta-carotene.

Another group of valuable components found in the endosperm includes the tocotrienols. Grams et al. (1970) discovered that in corn, tocotrienols were found only in the endosperm, whereas the germ contained most of the tocopherols. Tocotrienols can be extracted from plant material using various solvents. Processes for recovering tocotrienols from plant material are described by Lane et al. in U.S. Pat. No. 5,908,940, the entire disclosure of which is incorporated by reference.

Accordingly, the process described herein provides a nutritionally enhanced corn oil enriched with beta-carotene and optionally one or more other nutritional components.

Oil-based products made with corn oil obtained by the extraction method described herein can contain higher levels of important nutrients than similar products made with corn oil produced by conventional wet and dry milling processes. The corn oil obtained by the extraction methods described herein will include the corn oil from the germ and endosperm, and one or more other components extracted from the rest of the kernel. The one or more other components can be oil from the endosperm, tocotrienols, tocopherols, carotenoids, carotenes, xanthophylls, and sterols.

Tocopherols (vitamin E) and vitamin A are antioxidants and fat-soluble vitamins. When included in the diet, both have demonstrated health benefits. Blending of oil of the present invention with other oils or substances to achieve an appropriate level of beta-carotene, vitamin E, and tocotrienols is deemed within the scope of the present invention. In some embodiments, extracted corn oil prepared as described herein comprises about 140–250 ppm of tocopherol.

Oil produced in accordance with the present invention also may include approximately a 1.5 to 2 times increase in tocotrienol content over conventionally wet or dry milled crude corn oil. Using the method of optionally tempering, cracking and/or conditioning and extraction of corn, the corn oil is extracted and analyzed for tocotrienol content. The actual minimum and maximum values for tocotrienol content will depend upon the particular corn used.

The iodine value (IV) is a measure of an oil's relative stability toward oxidation. Generally, the lower the IV, the less susceptible the oil is toward oxidation and the longer it takes to oxidize the oil under test or use conditions. In addition, the greater the content of unsaturated fatty acids present in the oil, the higher the IV. Exemplary oils prepared according to the extraction method described herein generally possess IV values ranging about 123. The range of IV values is from about 120 to about 132 for the oils of this invention. Extraction of carotenes and xanthophylls and other pigments is described in detail by Blessin (*Cereal Chemistry*, 39, 236–242 (1962); the entire disclosure of which is incorporated by reference). Combinations of solvents, primarily ethanol and hexanes, can be used to extract carotenes and xanthophylls from corn. Ethanol, hexanes, other solvents, combinations, and ratios thereof may be used to produce oil of the present invention on a commercial scale.

A range of exemplary embodiments of the crude oil obtained according to the extraction method described herein generally possess the partial composition profile featured in Table 4.

TABLE 4

| Component | Range of Exemplary Extracted High Oil Corn | Extracted High Oil Corn (Range) |
|---|---|---|
| FFA (%) | 3.1–3.9 | 0.7–4.00 |
| C16:0 | 11.2–11.8 | 10–14 |
| C18:0 | 2.3 | 1.5–3.5 |
| C18:1, cis | 35–36 | 26–50 |
| C18:2, cis | 49 | 42–60 |
| C18:3 | 0.6–0.7 | 0.6–1.6 |
| Phosphorus (ppm) | 140–250 | 100–400 |
| Total Tocopherols (ppm) | 407–428 | 100–500 |

Fatty acids often found in the corn oil generally include palmitic, stearic, oleic, linoleic and linolenic acids.

The crude oil prepared according to the methods described herein can be subsequently partially or completely hydrogenated. Suitable methods for partially or completely hydrogenating oil are described in D. R. Erickson, Practical Handbook of Soybean Processing Utilization (1995, AOCS Press), the entire disclosure of which is hereby incorporated by reference.

When making oil-based products according to the invention, those products can include conventional corn oil, soy oil, canola oil, olive oil, palm oil, sunflower oil, safflower oil, antioxidant, flavoring, hydrogenated oil, partially hydrogenated oil and/or animal fat. By mixing the corn oil herein with one or more other oils, blended oil products are made. The corn oil-based products can also include materials such as food additives, salt, fat, food colors, β-carotene, annatto extract, curcumin or tumeric, β-apo-8'-carotenal and methyl and ethyl esters thereof, natural or synthetic flavors, antioxidants, propyl gallate, butylated hydroxytoluene, butylated hydroxyanisole, natural or synthetic tocopherols, ascorbyl palmitate, ascorbyl stearate, dilauryl thiodipropionate, antioxidant synergists, citric acid, sodium citrate, isopropyl citrate, phosphoric acid, monoglyceride citrate, anti-foaming agent, dimethyl polysiloxane, crystallization inhibitor, oxystearin, amino acids, vitamin, minerals, carbohydrates, sugars, herbs, spices, acidity regulators, firming agents, enzyme preparations, flour treatment agents, viscosity control agents, enzymes, lipids, and/or vegetable or animal protein. Additionally, these edible products can be enhanced or enriched with protein supplements containing utilizable protein. An exemplary food product such as a breakfast cereal could include ingredients such as meal of the invention, wheat and oat flour, sugar, salt, corn syrup, milled corn, dried fruit, vitamin C, B vitamins, folic acid, baking soda, and flavorings.

Other exemplary oil-based products that can comprise the oil prepared herein include food oil, cooking oil, edible oil and blended oil.

Equipment used for the extraction of oil from oilseeds, such as soybean and canola, can be used to prepare the corn oil and extracted corn meal described herein. Commercial-scale methods and equipment are sufficient for extracting corn oil from at least about 1 ton of corn per day. In some embodiments, the capacity of commercial-scale operations ranges from about 100 tons of corn per day to about 3000 tons of corn per day, or the capacity ranges from about 700 tons of corn per day to about 1700 tons of corn per day. Commercial-scale operations that process greater than about 3000 tons of corn per day are also sufficient.

Corn oil or corn meal quality is determined by evaluating one or more quality parameters such as the oil yield, phosphorus content, free fatty acid percentage, the neutral starch percentage, protein content, and moisture content. Any method can be used to calculate one or more of the quality parameters for evaluating the oil or meal quality.

The phosphorus concentration of crude oil can be determined using AOCS method Ca 12-55. AOCS method Ca 12-55 identifies the phosphorus or the equivalent phosphatide zinc oxide, followed by the spectrophotometric measurement of phosphorus as a blue phosphomolybdic acid complex. AOCS method Ca 12-55 is applicable to crude, degummed, and refined vegetable oils. The phosphorus concentration is converted to phospholipid concentration, i.e., gum concentration, by multiplying the phosphorus concentration by 30. In some embodiments, corn oil produced according to the invention includes about 100–400 ppm of phosphorus.

The free fatty acid percentage of oil can be determined using AOCS method Ca 5a-40. AOCS method Ca 5a-40 identifies the free fatty acids existing in the oils sample. AOCS method Ca 5a-40 is applicable to all crude and refined vegetable oils, marine oils, and animal fats. The neutral oil loss during processing is determined by adding the gum percentage and the free fatty acid percentage together. The amount of free fatty acid obtained in the extracted corn oil will depend upon the amount of fatty acids found within the corn from which the oil was extracted. In some embodiments, the free fatty acid content of the extracted oil ranges from about 0.70% by weight to 4.00% by weight.

Oil color can be determined using AOCS method Cc 13b-45. AOCS method Cc 13b-45 identifies the color of an oil sample by comparing the oil sample with known color characteristics. AOCS method Cc 13b-45 is applicable to fats and oils provided no turbidity is present in the sample. Color values are evaluated qualitatively by visual inspection of the oil. Generally, visual inspection results in an oil being classified as a light oil or a dark oil compared to a known oil color. Color values are quantitated by determining a red color value and a yellow color value using the AOCS method Cc 13b-45. Typically, crude corn oil isolated using conventional dry milling methods has a red color value ranging from about 7 to about 10 and a yellow color value ranging from about 60 to about 70. It is expected that corn oils isolated using cracking methods described herein will have oil colors that qualitatively are considered light and generally are lighter than crude corn oil derived from wet or dry milling techniques. The yellow color values may range from about 60 to about 70 and red color values may range from about 7 to about 10, as determined by AOCS Method Cc 13b-93.

The extracted corn oil can be used as a raw material for chemical modification, a component of biodegradable material, a component of a blended food product, a component of an edible oil or cooking oil, lubricant or a component thereof, biodiesel or a component thereof, a component of a snack food, a fermentation process raw material, and a component of cosmetics. Since the oil obtained by the extraction process herein has one or more components obtained from non-germ parts of the corn kernel, the oil is enhanced. In some embodiments, the oil will have an oleic range from about 20% to 80%, or preferably 25% to 50%, whereas yellow #2 corn has about 25% to 30% oleic acid in the oil. When making blended oils with the extracted oil, the blending can be done before, during or after the extraction process.

Biodiesel can be produced using the extracted corn oil of the invention. Biodiesel is a general term used for a variety of ester-based oxygenated fuels. Biodiesel produced today is a mixture of fatty acid methyl esters produced by methylating refined vegetable oil. Refined oil is preferable to crude oil or spent fryer oil due primarily to the quality of the glycerol by-product. The main drawbacks with previous biodiesel products and related vegetable oil lubricants are low temperature properties and reactivity toward oxidation and polymerization. A preferred biodiesel product comprises a low cloud point, reduced stearic and polyunsaturated fatty acid content, and high oleic acid content. Pour point correlates with low temperature properties and is influenced by the saturated fatty acid content of the oil. Polyunsaturated fatty acids are more susceptible to oxidation and polymerization reactions.

Solvent-extracted corn (SEC) oil exhibits improved cloud point performance over soy, while exhibiting similar chemical stability. Due to its higher level of oleic acid and lower level of linolenic acid, SEC oil is more stable compared to soy oil. Stability is defined herein as the ability of an oil to have a longer frying life, for cooking purposes.

TABLE 5

| Oil | % Palmitic (16:0) | % Stearic (18:0) | % Oleic (18:1) | % Linoleic (18:2) | % Linolenic (18:3) | % Erucic (22:1) |
|---|---|---|---|---|---|---|
| Rape | 3 | 1 | 14 | 12 | 7 | 49 |
| Canola | 4 | 1 | 60 | 20 | 9 | 2 |
| Soy | 8–10 | 4 | 19–28 | 53–56 | 6–10 | 0 |
| SEC | 11–12 | 2.3 | 35–37 | 49 | 0.6–0.7 | — |

SEC oil can be further processed to form lubricants such as by published procedures practiced currently in the industry (see, e.g., U.S. Pat. No. 6,174,501).

Meal produced from the cracking and oil extraction process described herein is useful for producing unique feed products. The corn meal used herein has been obtained after extraction of oil from whole kernels of corn, wherein the kernel has not been separated into its constituent part, although the kernel may or may not have been ground, cracked, chipped, or abraded. The process of removing the oil from corn via extraction serves to concentrate the remaining nutrients such as protein and essential amino acids.

Feed products containing predominantly corn meal produced by extraction require less supplementation with protein from other sources such as soybeans than feed products containing predominantly normal corn grain. The meal, by virtue of the composition arising from the processing method, offers feed manufacturers flexibility to produce feeds that could otherwise not be made. Animal feed rations having unique physical properties such as bulk density, texture, pelletability, and moisture holding capacity and/or unique nutritional properties are created by including the extracted corn meal of the present invention as a component of feed rations. The extracted corn meal isolated using cracking and extraction methods as described herein can, on its own, be a low-fat corn meal. Alternatively, it can be used in combination with other corn meals or nutritional components to make feed rations and food products. The extracted corn meal can also be combined with meals made from crops such as soybeans, canola, sunflower, oilseed rape, cotton, and other crops. The extracted corn meal can also be made from genetically modified corn and/or combined with meals made from transgenic oilseed grains to form an enhanced meal or enhanced product.

The extracted corn meal can be provided as a loose product or a pelleted product, optionally in combination with other components. For example, a pelleted product could include the extracted corn meal (by itself or in combination with other components) that has been pelleted and subsequently coated with zein protein. The corn meal can be included in blended meal products that can be provided in loose or pelleted form.

The feed rations prepared with the extracted corn meal will generally meet the dietary and quality standards set forth in the CODEX ALIMENTARIUS or by the National Research Council. The corn meal of the invention will generally comprise the components in the approximate amounts indicated in Table 6 below.

TABLE 6

| Component | Sample A Amount (%) | Sample B Amount (%) | Sample C Amount (%) |
|---|---|---|---|
| Moisture | 5–45 | 5–25 | 5–45 |
| Starch | 40–70 | 40–80 | 40–70 |
| Protein | 8–20 | 7–20 | 8–20 |
| Fat (Oil) | 0.75–8 | 0.75–6.0 | 0.75–12 |
| Crude Fiber | 2–6 | 2–4 | 2–4 |
| Ash | 1.5–3 | 0.5–2.0 | 1.0–3.0 |
| Lysine | 0.15–2.0 | 0.15–2.0 | 0.15–2.0 |
| Tryptophan | 0.03–2.0 | 0.03–2.0 | 0.03–2.0 |

The corn meals listed above may also further comprise unspecified amounts of the components for which no amounts have been indicated.

Varying levels of nutrients are required by different animals depending on species, age, and breed. Feed rations comprising different levels of nutrients are made by subjecting the corn to different degrees of extraction, i.e., more oil is removed from the corn by subjecting it to extraction to a greater degree. Therefore, feed rations comprising the extracted corn meal of the invention can be made to include different amounts of fat, protein, and carbohydrates by controlling the extent to which the corn is extracted. Table 7 details the amounts in which the indicated ingredients are present in animal feed rations comprising the extracted corn meal, the specific inclusion range being indicative of exemplary rations in which extracted corn meal is a main ingredient and the general inclusion range being indicative of rations in which one or more other ingredients, for example, carbohydrate-based energy sources such as sorghum, wheat, and/or other cereal grains or their by-products, or other non-cereal grain ingredients, may be included.

TABLE 7

| Ingredient | General Inclusion Range | Exemplary Inclusion Range |
|---|---|---|
| Corn meal described herein | 2–95% | 50–90% |
| Oilseed Meal[1] | 3–35% | 10–30% |
| Meat and Bone Meal | 0–12% | 0–7% |
| Feather Meal | 0–6% | 0–4% |
| Fat | 0–10% | 1–6% |
| Salt | 0.1–0.5% | 0.1–0.5% |
| Lysine | 0–0.4% | 0–0.4% |
| Methionine | 0–0.3% | 0–0.3% |
| Nutrient Premix | 0–1.0% | 0–1.0% |

[1]Oilseed meal can consist of, but is not limited to, soy, sunflower, canola, cottonseed, and other plant-based meals, which themselves may or may not have been subjected to an oil extraction process.

Meat and bone meal is obtained from suppliers such as Darling International, Inc. (Irving, Tex.). Oilseed meal is obtained from suppliers such as Cargill Oilseeds (Cedar Rapids, Iowa). Feather meal is obtained from suppliers such as Agri Trading Corp., (Hetchinson, Minn.). Amino acids are obtained from suppliers such as DuCoa, (Highland, Ill.).

Feed rations are made by mixing various materials such as grains, seed meals, vitamins, and/or purified amino acids together to form a composite material that meets dietary requirements for protein, energy, fat, vitamins, minerals, and other nutrients. The mixing process can include grinding and blending the components to produce a relatively homogeneous mixture of nutrients. Physical properties of the feed raw materials and of the compounded feed affect the nutritional quality, storability, and overall value of the products. Suitable processes for manufacturing feed rations are disclosed in Feed Manufacturing Technology IV (1994, American Feed Industry Association) and incorporated herein in its entirety.

The extracted corn meal may be somewhat analogous to steam-flaked corn in terms of digestibility of the starch fraction, but may have better digestibility in ruminants by virtue of the processing conditions. As discussed herein, specific oil levels can be achieved in the extracted meal by altering processing conditions. The protein, amino acid, and oil levels of the present extracted meal cannot be achieved in steam-flaked normal corn, and steam-flaked high oil corn may have too much oil, which could adversely affect ruminant animal health.

Many types of animal feed rations can be developed using extracted corn meal of the present type, and for illustration purposes, the following diet types will be described herein: (1) meal made from corn grain wherein the corn grain has an oil content of from about 3% by weight to about 30% by weight and a protein content of about 9% by weight, and meal resulting from this corn has an oil content of from about 1% by weight to about 18% by weight and preferably about 6% by weight, for use in a hog finishing diet; and (2) meal made from corn grain wherein the corn grain has an oil content of from about 3% by weight to about 30% by weight and a protein content of about 9% by weight, and meal resulting from this corn has an oil content of from about 1% by weight to about 18% by weight and preferably about 4.0% by weight, for use in a poultry broiler diet.

Extracted corn meal of the present invention has several advantages over meal from yellow #2 corn when used as an ingredient in aquaculture feed products. In agriculture, pigments such as carotenoids in feed are often deposited in fatty tissue when consumed resulting in an undesirable color. For some aquaculture species, consumer preference is for very light colored tissue. In other species, such as salmon, consumer preference is for a pink or red tissue. An advantage of extracted corn meal in aquaculture diets is that some undesired pigments will be reduced by virtue of the process to produce extracted corn meal; the solvent-soluble pigment compounds (such as carotenoids) are removed from the meal and concentrated in the oil. A second advantage of extracted corn meal over dry-milled or wet-milled corn meal products is the improved protein content and quality, since the oil has been substantially removed from the kernel resulting in a meal product in which the protein has been concentrated. Because the meal is obtained from all portions of the kernel, including most or the entire embryo, the proteins are generally of higher quality and quantity than would be found in extracted corn grits. By including extracted corn meal in aquaculture feeds, it will be possible to raise animals with fewer undesirable pigment compounds in the tissue.

Solvent extracted corn meal is also useful for fermentation-based production of compounds, such as, for example, ethanol, lactic acid, and vitamins. Solvent extracted corn meal from corn can be hydrolyzed to provide soluble sugars. The meal serves as a carbon and nitrogen source for bacterial, fungal, or yeast cultures. Biotin and other vitamins can be produced through the cultivation of microorganisms. Organisms can include *Pseudomonas mutabilis* (ATCC 31014), *Corynebacterium primorioxydans* (ATCC 31015), Arthrobacter species, Gibberella species, Penicillium species, or combinations thereof.

Nutrients used in the cultivation of these and other microorganisms include, for example, starch, glucose, alcohols, ketones, and as a nitrogen source, peptone, corn steep liquor, soybean powder, ammonium chloride, ammonium sulfate, ammonium nitrate, extracted corn meal, or urea. Various salts and trace elements may also be included in media for the culture of microorganisms. The pH of the culture medium is about 4 to about 9, preferably about 6 to about 8 and most preferably about 7 for bacterial species. The pH is about 5 to about 7 for mold or yeast. During cultivation, temperatures are kept between 10° C. to 100° C., preferably between about 20° C. to about 80° C., more preferably between about 20° C. to about 40° C., and most preferably about 25° C. Biotin production is described in U.S. Pat. No. 3,859,167, incorporated herein by reference. Cis-tetrahydro-2-oxo-4-n-pentyl-thieno[3,4-d]imidazoline is added to a culture medium containing solvent extracted corn meal and other appropriate identified ingredients in combination with a microbial species capable of forming biotin. In general, the microorganism is cultivated for about 1 to 10 days, preferably about 1 to 8 days, and more preferably about 2 to 7 days, after which time biotin is separated and purified. In one embodiment, to purify biotin, cells are removed from the culture medium; the filtrate is absorbed on activated charcoal and purified with an ion exchange column. Alternative methods of purification are also used such as crystallization by adjusting the pH of the biotin-contained solution to near its isoelectric point.

Solvent extracted corn meal can also be further processed to produce biodegradable materials. For instance, the meal of the present invention may be incorporated as a thermoplasticising agent. The meal of the invention may be included in the methods described in U.S. Pat. No. 5,320,669, which is incorporated herein by reference. The thermoplastic material is prepared using solvent extracted corn meal, as obtained from the process described herein. In one embodiment, the biodegradable thermoplastic composition prepared using the meal of the present invention is treated with an organic solvent, and optionally a cross-linking agent, to link together the starch and protein of the extracted corn grain. The cross-linking agent referred to herein may be any compound capable of linking the starch and the protein, such as, for example, an aldehyde, an acid anhydride or an epoxide. The compositions so formed using the meal of the present invention can be used to make extruded or molded articles that are biodegradable, water-resistant, and/or have a high level of physical strength.

Blended products comprising the extracted corn meal and one or more other oilseed meals are made by one or more of the following ways: 1) combining the corn and the other oilseed prior to cracking and subjecting the entire seed mixture to the extraction process described herein to form a blended meal; 2) combining the corn and the other oilseed after cracking and conditioning and subjecting the entire seed mixture to an extraction process as described herein to form a blended meal; 3) combining the extracted corn meal with extracted or non-extracted other oilseed meal to form a blended meal; or 4) combinations thereof to form a blended meal. At any time during these processes, additional components can be added to the blended meals to form a blended product.

The extracted corn meal can also be used in foodstuffs such as snack food, blended food products, breads, fermentation feedstock, breakfast cereals, thickened food products such canned fruit fillings, puffed or extruded foods, and porridge. When used in edible products for humans or animals, the extracted corn meal can be combined with other components such as other meal, other oilseed meal, grain, other corn, sorghum, wheat, wheat milled byproducts, barley, tapioca, corn gluten meal, corn gluten feed, bakery byproduct, full fat rice bran, and rice hull.

The extracted corn meal can also be used as a raw material for production of corn protein isolates, for fermentation, for further chemical processing, in addition enzymes, such as an amylase, a protease, a cellulase, an esterase or a liginase, can be added to the meal to help facilitate the breakdown of starch and proteins.

The extracted corn meal is optionally subjected to conventional methods of separating the starch and protein components. Such methods include, for example, dry milling, wet milling, high pressure pumping or cryogenic processes. These and other suitable processes are disclosed in Watson, S. A. & P. E. Ramstad, ed. (1987, Corn: Chemistry and Technology, Ch. 11 and 12, American Association of Cereal Chemist, Inc., St. Paul, Minn.), the disclosure of which is hereby incorporated by reference. Due to the prior removal of oil from the corn meal, the starch and protein components of the extracted corn meal are separated from other components more easily than they would be if the corn oil were not extracted.

Several important quality parameters for the extracted meal include the fat, starch, protein, and moisture content. Methods for evaluating quality parameters of oilseed meals are disclosed in the AOCS methods, the relevant disclosure of which is hereby incorporated by reference. These methods can also be applied to the extracted corn meal prepared as described herein.

Corn meals derived using different methods or isolated at different times are compared by normalizing the meals to a common moisture content. The moisture content of an oilseed protein concentrate, such as a corn meal or whole corn, is determined using AOCS method Ba 2b-82. The crude fiber content of corn meal is determined using AOCS method Ba 6-84. AOCS method Ba 6-84 is useful for grains, meals, flours, feeds and all fiber bearing material from which the fat can be extracted leaving a workable residue. The average crude fiber content for the corn meal of the invention is 2.0%. Crude protein content of corn meal is determined using AOCS method Ba 4e-93 or AOAC 990.03. The starch content of corn meal is determined using the AACC Method 76–11 (glucoamylase method). This method may be modified with the following changes: weigh 0.1 g of sample into a culture tube instead of 1 g of sample into an E-flask; and extract free sugar before enzyme digestion.

The analytical methods provided herein are illustrative examples of useful methods for computing various quality parameters for the oils and meals described herein. Other suitable methods are known and may be used to compute the quality parameters disclosed and claimed herein.

The following examples are included to demonstrate specific embodiments of the invention. It should be appreciated by those of skill in the art that the techniques disclosed in the examples which follow represent techniques discovered by the inventors to function well in the practice of the invention, and thus can be considered to constitute exemplary modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

This example describes a continuous solvent extraction process in the context of the present invention. The extraction process consisted fundamentally of four parts: preextraction, extraction, meal desolventization, and oil desolventization. These various stages are described in further detail below.

Whole kernel corn (approximately 3% oil) was tempered to nominally 14.5% moisture by adding water to "as is" moisture corn in a 350 liter Toronto Coppersmithing Toreo Model R-12 ribbon blender. Water was sprayed into the vessel at a rate of 2 liters/hr. After the appropriate amount of water was added, the corn was stirred for another hour and allowed to soak for 24 hours before being tested for moisture.

The tempered corn, at ambient temperature, was then cracked using a Roskamp (Waterloo, Iowa) 6.5 series double stand cracking roll. Both top and bottom rolls were set such that one roll rotated faster than the other. The fast rolls on both the top and the bottom rolls rotated at 1065 revolutions per minute (rpm) with 6 spiral RBV cut corrugations per inch. The slow rolls were cut identically but rotated at 708 rpm. The roll diameters were 9 inches; the roll length was 12 inches. Crack moistures were about 13.3 to 15.7%. Cracks of the following average particle size distribution ranges were generated: 15.9% retained by US #4 mesh screens, 39.9% retained by US #6 mesh screens, 27.8% retained by US #8 mesh screens, 6.8% retained by US #10 mesh screens, 4.3% retained by US #18 mesh screens, and 5.3% pass through US #18 mesh screens.

The cracked corn particles were conditioned using a steam jacketed screw conveyor manufactured by Scott Equipment Company (New Prague, Minn.), model TB1814 Tender Blend 18" screw diameter and 12 feet in length. There were 3 blades sweeping the perimeter of the inside of the screw. Paddles were approximately 3 inches wide by 4 inches in length. The screw rotated at 4 rpm. The jacketed side of the conveyor was fed 30 psig saturated steam. Exit temperature was monitored and adjusted to 80° C. (175° F.).

A continuous 150 kg/hr. Crown (Roseville, Minn.) model II pilot extractor was used to process the cracked corn. This pilot scale extractor utilized mixed hexanes as a solvent with 5 counter-current miscella wash zones and a tail wash section. Six-miscella recirculation pumps were utilized. Fresh hexane at about 50° C. to about 60° C. was fed in the upper portion of the extractor. The dimensions of the extractor were about 29 feet long, 7.8 inches wide, and 4.5 inches deep. Of the total length 23 feet were wetted and 19.5 feet of that were subjected to wash. The average feed rate was approximately 75 kg/hr. The residence time was approximately 60 minutes. The solvent-to-corn cracks ratios were adjusted between 0.75:1 and 1.33:1. Full miscella was sent to the oil desolventization system at 27° C. to 34° C.

Ambient and indirect heat desolventization was done first in a Schnecken (Crown Iron Works, Roseville, Minn.) steam jacketed conveyor (SJC). The SJC consisted of a hollow flight screw inside of a steam jacket. It was 12 feet long and 10 inches in diameter. The open flight screw created a tumbling action as it conveyed the extracted material through the conveyor. This ensures that all material was exposed to the heated wall. A pneumatic controller regulated the amount of steam supplied to the jacket. The temperature at the outlet of the conveyor was monitored and used as the basis for the control of steam supplied to the jacket. Vapors from the conveyor were collected in the low vacuum condenser by the slight negative pressure developed by the system fan. A double-deck nominal 100 kg-capacity desolventizer and toaster (DT) with sweep arm agitation was utilized. Dimensions were 36 inches in diameter, 20 inches high per deck. Steam sparge was piped through the top sweep arm only. Meal exit moistures ranged from about 9.4% to about 17.7%, and exit temperatures ranged from 57° C. to 104° C.

Hexane recovered from the SJC and extractor was condensed, dewatered, and recycled to the extractor.

Oil desolventization was executed using a rising film evaporator (RFE). This unit consisted of sixteen 1.5 cm diameter tubes inside a large jacket. The jacket was filled with steam, which heats the tubes. The extract-laden liquid (normally oil in hexane called miscella) was pumped into the bottom of the tubes. As it traveled up the inside of the tubes, steam heat caused the liquid to boil. The vapors hold the liquid against the wall of the tube in a thin, rising film. At the top the liquid and vapor are allowed to separate. The oil flowed into an overflow pipe to the oil stripper (OS), while the vapors were carried over to a condenser. The tubes were under vacuum so that the liquid boiled at a low temperature. The oil stripper was a disc and donut style distillation column. The liquid was spread out in a thin film over a disc and dripped down onto a donut back onto a disc. Thus the oil cascaded down the column. At the same time, steam was injected into the bottom of the stripper. This steam passed over the liquid film removing the solvent remaining in the liquid. A steam jacket to keep the liquid and steam hot surrounded the disc and donut column. The oil stripper was also under vacuum and the vapors (solvent and steam) goes to the same condenser as the RFE vapors. The stripping steam passed through a demister to remove water droplets before going into the OS.

Hexane recovered from the rising film evaporator and the OS was condensed, dewatered, and recycled to the extractor.

Although this example illustrates use of corn with an oil content of about 3% by weight oil, the same process can be used for corn with an oil content of about 3% by weight to about 30% by weight.

EXAMPLE 2

This example sets forth one method of recovering lighter particles such as fines, generated during the cracking step from the processing of high oil corn.

Whole kernels from corn are cracked using a standard cracking mill roller such as Roskamp 6.5 Series, (Roskamp, Waterloo, Iowa). During this cracking step an air stream is provided wherein the velocity of the air stream is controllable. The air stream is directed to pass across the cracking mill roller and the velocity of the air stream is regulated such that the smaller and lighter particles are carried away in the air stream, hence separating them from the heavier cracks. The lighter particles are then recovered by standard process equipment such as a baghouse. The recovered lighter particles are then introduced into starch-containing product streams for the recovery of starch.

Although this example uses corn with an oil content of about 3% by weight, the same process can be used for corn with an oil content of from about 3% by weight to about 30% by weight.

EXAMPLE 3

This example sets forth one method of recovering lighter particles such as fines, generated during the cracking step from the processing of whole kernel corn.

Whole kernels from yellow #2 corn are cracked using a standard cracking mill roller such as Roskamp 6.5 Series, (Waterloo, Iowa). During this cracking step, a controlled air stream is directed to pass across the cracking mill roller, and the velocity of the air stream is regulated such that the smaller and lighter particles are carried away in the air stream, hence separating them from the heavier particles. One such example of the controlled air stream is provided by a Crown™ multi-stage aspirating system operated at 2600 cubic feet per minute. The lighter particles are recovered by standard process equipment such as a baghouse. The recovered lighter particles are introduced into starch-containing product streams for the recovery of starch or can be sold separately for animal feed. Although this example uses corn with an oil content of 3% by weight, the same process can be used for corn with an oil content of from about 3% by weight to about 30% by weight.

EXAMPLE 4

This example sets forth a method for the recovery of fines generated during the cracking step from the processing of whole kernel corn.

Corn is processed as described in Example 1. The conditioned corn prior to cracking and the corn cracks are sprayed or misted with a source of liquid providing broad enough coverage to physically eliminate the lighter, airborne particles. Water or oil is used as the liquid. The oil can be, e.g., extracted oil from the corn or from another source such as vegetable oil. Alternatively, the liquid spray can be a substance that adds value to the resulting meal as well as recovers the value from the fines. The liquid spray is typically pure water, process water or water that has been supplemented with nutritional additives such as vitamins, oil or minerals. The liquid stream containing the particulates is carried away from the heavier particles in each case and is collected. The particulates are separated from the liquid using standard process equipment including a hydrocyclone or centrifuge. Optionally, the recovered fines may be dried before further use. The recovered lighter particles are then introduced into starch-containing product streams for the recovery of starch or can be sold separately for animal feed.

Although this example was performed using corn with an oil content of about 3% by weight, the same process can be used for corn with an oil content from about 3% by weight to about 30% by weight.

EXAMPLE 5

This example sets forth a method to reduce fine particle generation using a single cracking roll.

Corn grain (9.5% by weight oil) was passed through a Roskamp 6.5 Series Cracker in which only the top set of rollers was used. The roll gap was varied between 0.088 and 0.052 inches. To better understand the effects of moisture on the amount of fines generated, two different grain moisture levels were studied at the various roll gap settings indicated above. Moisture levels were about 12.7% and about 16.4% (moisture levels were measured by Mettler Toledo Model HR73).

For each test, 25 pounds of the corn grain was used. Particle sizes were measured by screening the cracked grain through US mesh sieves (manufactured by W. S. Tyler). The cracks were separated by #4 (4.75 mm), #8 (2.36 mm) and #18 (1 mm) screens. The amount of fines was determined as that material that passes through the #18 mesh screen.

Table 8 summarizes the results of the trials.

TABLE 8

| Trial Number | Moisture (%) | Rolls | Gap Setting (inches) | % by Weight on top of #4 mesh | % by Weight on top of #8 mesh | % by Weight top of #18 mesh | % by Weight in base < #18 mesh |
|---|---|---|---|---|---|---|---|
| 1 | 12.67 | Single | 0.088 | 60.7 | 35.2 | 2.2 | 1.8 |
| 2 | 12.72 | Single | 0.088 | 69.5 | 26.8 | 2.4 | 1.4 |
| 3 | 16.38 | Single | 0.088 | 86.8 | 11.8 | 1.0 | 0.3 |
| 4 | 12.67 | Single | 0.052 | 49.6 | 43.1 | 4.2 | 3.2 |
| 5 | 16.38 | Single | 0.052 | 80.5 | 16.5 | 1.6 | 1.3 |

The roller gap setting at 0.088 inches are an average for the lower moisture level 12.67 and 12.72%) of 65.1% cracks retained on the #4 screen, 31% on the #8 screen, 2.3% on the #18 and 1.6% as fines. At the higher moisture level (16.38%), the 0.088 inch roller gap setting yielded 86.8% cracks on #4 screen, 11.8% on #8 screen, 1.0% on the #18 and 0.3% as base fines.

The trials at a tighter gap setting (0.052 inch) yield slightly different results as compared to the gap setting of 0.088 inch for the 12% moisture level. The amount of material left on the #4 screen drop 15%, the #8 screen drop 12%, the #18 screen increases 1.9% and the base (fines) increase 1.6%. Similar results were observed for the 16% moisture levels between the 0.088 and 0.052 inch roller gap settings (0.3 vs. 1.3% fines, respectively).

Cracked corn produced using a single set of cracking rolls had an acceptable amount of fines for use in the extraction process. However, the tests illustrate about a 2–4 fold decrease in the level of fine material as the moisture level of the grain increases from 12 to 6%.

EXAMPLE 6

This example sets forth the use of double roll cracking as a means of reducing the amount of fines generated during the cracking process.

Corn grain (9.5% by weight) was passed through a Roskamp 6.5 Series Cracker in which both sets of rollers were used. The gap settings for the top and bottom roll were varied. For the "wide" gap settings, the top roller was set at 0.106 inches and 0.088 inches for the bottom roller. For the "narrow" settings the top roller was set at 0.075 inches and the bottom roller was set at 0.052 inches.

For each test, 25 pounds of the high oil corn grain was used. Particle sizes were measured by screening the cracked grain through US mesh sieves (manufactured by Ws Tyler). The cracks were separated by #4 (4.75 mm), #8 (2.36 mm) and #18 (1 mm) screens. The amount of fines was determined as that material that passed through the #18 mesh screen. Moisture levels were about 12.7% and about 17% (moisture levels are measured by Mettler Toledo HR73).

Table 9 summarizes the results of the trials.

TABLE 9

| Trial Number | Moisture (%) | Roll setting | Gap Setting (inches) | % by weight on top of #4 mesh | % by weight on top of #8 mesh | % by weight top of #18 mesh | % by weight in base < #18 mesh |
|---|---|---|---|---|---|---|---|
| 1 | 12.67 | Wide | 0.106/0.088 | 28.0 | 60.2 | 7.6 | 4.2 |
| 2 | 16.99 | Wide | 0.106/0.088 | 46.5 | 41.5 | 6.4 | 4.0 |
| 3 | 12.67 | Narrow | 0.075/0.052 | 13.8 | 69.9 | 12.0 | 3.8 |
| 4 | 12.72 | Narrow | 0.075/0.052 | 29.4 | 56.6 | 9.9 | 4.0 |
| 5 | 16.99 | Narrow | 0.075/0.052 | 43.1 | 46.4 | 6.4 | 4.0 |
| 6 | 16.50 | Narrow | 0.075/0.052 | 45.2 | 38.1 | 9.5 | 7.0 |

The results indicate that at the 12% moisture level there was not a significant difference between the two different roller gap settings tested. On average the wide settings yield 28% on the #4 screen, 60.2% on the #8 screen, 7.6% on the #18 screen and 4.2% passed through to the base. Whereas at approximately the same moisture level but with the narrow roller gap settings, 28.5% was collected on the #4 screen, 63.3% on the #8 screen, 11% on the #18 screen and 3.9% pass through to the base.

The results at the higher moisture level (~16–17%) indicate that both the wide and narrow settings yielded similar results. Therefore with the double roll cracking there does not seem to be an effect with moisture level on fines generation as with the single roll cracking.

The results indicate that the double cracking rolls increase the base level of fines as compared to single roll cracking. Both the single and double roll cracking produce an acceptable amount of fines for use in the extraction process as described in Example 1.

EXAMPLE 7

This example sets forth the use of solvent extracted corn meal from the current invention as a rich source of starch for ethanol fermentation. One method to provide soluble sugars suitable for fermentation is to hydrolyze starch molecules, which are included in the solvent extracted corn meal. Two samples of about 300 grams of corn meal were prepared according to the present invention. Sample 1 was prepared from corn with an initial grain oil content of 8.7% yielding a meal oil content of 5%. Sample 2 was prepared from corn with an initial grain oil content of 12.5% yielding a meal oil content of 7.5%. Also, 300 grams of yellow #2 corn starch was prepared by conventional wet milling methods from grain having an oil content of 3.7%. Each sample passed through a 1 mm screen using a Retsch Mill and combined with 700 ml of 99° C. to 100° C. water and 0.5 ml α-amylase in a sealed container. The pH was adjusted to 5.9 with base. The mixtures were stirred for 45 minutes at the same temperature and additional α-amylase enzyme was added. After an additional 45 minutes of incubation, the pH of the mixtures was adjusted to 4.5 with acid. Half a milliliter (0.5 ml) glucoamylase (Optimax 7525) and 0.5 g protease (Fungal Protease 5000) were added and incubated with both enzymes at 62° C. for 22–24 hours. Throughout the procedure, the degree of starch hydrolysis was monitored by HPLC (Waters 2690 Separations module) using an organic acid column (Aminex HPX-87H Ion Exclusion Column, 300 mm×7.8 mm, Bio Rad).

Total nitrogen content for each sample was determined by Leco 2000 CN. Free amino nitrogen (FAN) is determined by the AOAC method ($15^{th}$ ED. 1990. pg. 735).

Forty-five grams (45 grams) of enzyme-treated solvent extracted corn meal (targeting approximately 20% carbohydrate) were added to 125 ml flasks. In addition, separately, solvent extracted corn meal was added to 125 ml flasks to give dextrose concentrations of 120 gm/L in 48 g total culture media. Yeast extract (Difco) was added at 1 gm/L to ensure that nitrogen was not limiting. Cultures were inoculated with 10% inoculum from overnight yeast cultures (a typical Altech ethanol yeast of *Saccharomyces cerevisiae*) and incubations proceeded for 40 hours at 30° C. on a rotary shaker at 125 rpm. Ethanol production was monitored by HPLC.

TABLE 10

Amount of Dextrose Liberated from Starch by Milling; Amount of Available Nitrogen

| Corn Sample | Calculated[1] Initial Dextrose content (gm/L) | Dextrose[2] (gm/L) | % Starch Hydrolysis | FAN[2] (ppm) | Total Nitrogen[2] (ppm) |
|---|---|---|---|---|---|
| 1 (Extracted Corn Meal) | 220.9 | 197.8 | 89.6 | 419.6 | 5152 |
| 2 (Extracted Corn Meal) | 228.1 | 193.5 | 84.8 | 337.4 | 4896 |
| Yellow #2 | 251.94 | 175.6 | 69.70 | 223.8 | 2992 |

[1]Calculated based on starch content and chemical gain of 1.11
[2]Indicates as is values obtained from 30% starch hydrolysate Media for fermentations were normalized on a weight basis (45 grams), which resulted in starting dextrose concentrations of 133–233 gm/L. Ethanol productivity (gm/L/h) at 24 hours for sample 1 was 3.04 and for sample 2 was 3.11. Ethanol productivity (gm/L/h) at 24 hours for yellow #2 corn at 24 hours was 2.90. The ethanol yield (%) for sample 1 was 38.5 and for sample 2 was about 40.2. The ethanol yield (%) for yellow #2 corn was 41.7.

TABLE 11

Ethanol Conversion and Productivity

| Corn Sample | Ethanol conversion (%) | | | Ethanol productivity (gm/L/h) | | |
|---|---|---|---|---|---|---|
| | 15 Hrs | 24 Hrs | 40 Hrs | 15 Hrs | 24 Hrs | 40 Hrs |
| 1 (ECM) | 48.65 | 42.42 | 35.16 | 3.10 | 1.66 | 0.80 |
| 2 (ECM) | 37.24 | 38.00 | 34.14 | 3.16 | 2.01 | 1.08 |
| Yellow #2 | 43.22 | 43.41 | 41.06 | 3.18 | 2.00 | 1.14 |

Starting dextrose concentrations for yeast cultures were equalized to approximately 120 gm/L. The ethanol yield (gm/L) after 24 hours for sample 1 was 42.4 and for sample 2, 38.0. The ethanol yield (gm/L) for yellow #2 corn after 24 hours was 43.1. Ethanol productivity (gm/L/h) of sample 1 at 15 hours and 24 hours was 3.10 and 1.66, respectively. Ethanol productivity of sample 2 at 15 hours and 24 hours was 3.16 and 2.01 respectively. The ethanol productivity of yellow #2 corn at 15 hours and 24 hours was 3.50 and 2.00, respectively.

TABLE 12

Ethanol Conversion and Productivity

| Corn Sample | Ethanol conversion (%) | | | Ethanol productivity (gm/L/h) | | |
|---|---|---|---|---|---|---|
| | 15 Hrs | 24 Hrs | 40 Hrs | 15 Hrs | 24 Hrs | 40 Hrs |
| 1 (ECM) | 45.30 | 38.54 | 40.03 | 5.73 | 3.04 | 1.90 |
| 2 (ECM) | 41.56 | 40.21 | 37.50 | 5.15 | 3.11 | 1.74 |
| Yellow #2 | 45.00 | 41.72 | 40.37 | 5.03 | 2.90 | 1.70 |

Although this example is directed to ethanol fermentation, the solvent extracted corn meal of the present invention can also be used as a starch source for other fermentation products. Enzymes can be used to convert the starch and protein matrix of corn meal into simple sugars suitable for fermentation. Suitable enzymes include, but are not limited to, amylase(s) (e.g., glucoamylase), proteases, cellulase(s) (e.g., xylonase), esterase(s) (e.g., ferulase, acetylesterase) and ligninase(s).

EXAMPLE 8

This example sets forth the use of solvent extracted corn meal from the current invention as a rich source of starch for the fermentative production of citric acid. The production of citric acid from de-fatted corn meal involves several steps including starch hydrolysis, as described in Example 7, fermentation, and citric acid recovery.

Once the starch from solvent extracted corn meal is suitably prepared through treatment with enzymes as described in Example 7, the solution is filtered and demineralized according to commonly known practices. Resulting sugars are brought to a solids content of about 120 mg/l with demineralized water in a deep-tank fermentation vessel. The deep tank method is also known as the submerged process. In this method the tank is supplied with sterile air, nutrients and a carbon source, (hydrolyzed starch), and innoculated with *Aspergillus niger* spores. Spores of the fungus in a concentration of about 100 spores per liter of culture liquid, which corresponds to an amount of 10 to 15 g of spores per cubic meter ($m^3$), would be added to the nutrient solution and the citric acid production would be carried out by the fungus. Examples of *A. niger* strains are ATCC 1015 described in U.S. Pat. No. 2,492,667, and DSM 5484 described in U.S. Pat. No. 5,081,025, the disclosures of which are incorporated by reference.

The incubation of the broth thus inoculated would be carried out at conditions generally known and described for citric acid production, such as continued aeration and temperature control. During the fermentation process, the temperature would be maintained at about 90° F., the pH would be maintained at about 2 to 3 with sodium citrate, and sterile air would be added to maintain about 50% dissolved oxygen content. Fermentation would be carried out until the fermentation broth reaches a reducing sugar content of about 1 g/L, which may require several days to achieve. Two main separation processes can be used in the recovery of citric acid, the Lime-Sulfuric Acid process and the Liquid extraction process. The Lime-Sulfuric Acid method is commonly used and is familiar to those skilled in the art of citric acid production.

EXAMPLE 9

This example sets forth the use of extracted corn meal in an aquaculture feed product.

Two feeding programs are used for two species of fish: tillapia and catfish. One feeding program utilizes a feed including corn grits produced from dry-milled yellow #2 corn. The other feeding program utilizes a feed including extracted corn meal derived from the current invention. Feeds are produced with the following ingredients:

TABLE 14

| Ingredient | Percent |
|---|---|
| Herring Fishmeal | 8 |
| Soybean Meal | 50 |
| Corn | 34.3 |
| Wheat Middlings | 5 |
| Dicalcium Phosphate | 1 |
| Vitamin Mix | 1.5 |
| Trace Mineral Mix | 0.2 |
| Crude Protein (N × 6.25) | 32 |

In the feed ration described in Table 14, extracted corn meal (ECM) can be substituted for some or all of the corn, some or all of the wheat middlings, and/or some of the soybean meal at various levels to produce a desired nutrient profile that can vary depending on the fish species to be fed.

One group of tillapia is fed feed containing extracted corn meal. A second group of tillapia is fed feed containing corn grits. Similarly, one group of catfish is fed feed containing extracted corn meal, and one group of catfish is fed feed-containing corn grits. The experimental design includes four ponds per treatment of one hundred fish per pond, for a total of sixteen ponds and 1,600 fish. Fish within species and ponds are of similar size and weight. Within each species and treatment, fish are fed amounts of feed necessary to support growth rates typical in commercial aquaculture production. Fish are raised from fingerling size to a suitable size reflective of typical market weights, for example, to about one and a half pounds.

Fish are caught and processed in a manner to produce fillets that are compared visually. The effect of extracted corn meal on meat quality is evaluated by measuring the color of the tissue using a color reference guide. A trained and experienced sensory panel is used to evaluate the consumer preference factors such as color and appearance.

The process to produce extracted corn meal separates some of the solvent soluble pigments from the meal portion.

Therefore, fish fed with extracted corn meal receive less of these pigments in their diet than fish fed a diet containing corn. Pigments such as carotenoids can be deposited in tissue when consumed in the diet. Therefore, fish fed diets containing extracted corn meal will have lighter colored tissue than fish fed diets containing corn. Growth of fish raised on diets containing extracted corn meal would be similar to fish raised on diets containing corn, but adjustments to the proportions of ration ingredients may need to be made to account for differences in starch digestibility, amino acid availability, and fatty acid content.

EXAMPLE 10

This example sets forth the use of oil from the current invention as a source of an improved biodiesel fuel.

In a continuous process, approximately 62 kg/hr (137 lbs/hr) of oil extracted from cracked corn of the current invention and refined according to known industry processes, is mixed with 18 kg/hr (40 lbs/hr) of methanol in a stirred tank reaction unit. Simultaneously 0.08 kg/hr (0.1775 lbs/hr) of sodium hydroxide is added to the same stirred tank reaction unit, which operated at 20 psig and approximately 80° C. These conditions provide essentially 100% conversion of added triglycerides to fatty acids and methyl esters.

The two phases of the reaction mixture are allowed to stand and separate to provide methyl esters in the upper phase, and a mixture of glycerol and approximately 10–15% by weight residual methyl esters, methanol, and base in the lower phase. Approximately 6.4 kg/hr (14 lbs/hr) of the glycerol phase is neutralized, present methanol flashed off, and the remainder is sent to a continuously stirred reaction unit, operated at 80° C. and 320 psig. The reaction unit also contains approximately 4% by weight Amberlyst-15 catalyst with a residence time of 2 hours and approximately 7.9 kg/hr (17.5 lbs/hr) iso-butylene is fed to the reaction unit. The biodiesel fuel is produced at approximately 66 kg/hr (145 lbs/hr) and has a kinematic viscosity and cloud-point that is greater than biodiesel without glycerol ethers present.

EXAMPLE 11

This example sets forth the use of meal derived from corn processed through cracking and extraction as a component of a hog finishing feed ration. This example details a comparison of two different feed rations: a first feed ration containing normal corn that has not been solvent extracted and a second feed ration containing extracted corn meal. The feed ration containing extracted corn meal is used when lean pork meat is a desired end product. Table 15 shows a comparison of swine feed rations made using normal corn (not solvent extracted) and extracted corn meal obtained from the current invention comprising about 4.0% by weight or less of oil (fat). The feed ration is generally produced by blending, mixing, and pelleting the ingredients to produce a feed product; however, one or more of these steps can be omitted in the process of preparing the feed ration. Amounts are expressed on an "as is" or "as fed" moisture level.

TABLE 15

Swine Finishing Feeds

| Ingredients | Traditional Corn Feed (% by weight) | Extracted Corn Meal Blend (%) |
|---|---|---|
| Corn | 79.98 | — |
| Extracted corn meal (~4.0% oil) | — | 83.55 |
| Soybean meal | 12.45 | 6.60 |
| Meat & bone meal | 6.59 | 7.22 |
| Feather meal | — | — |
| Fat | 0.10 | 1.50 |
| Salt | 0.40 | 0.70 |
| Lysine | 0.08 | 0.15 |
| Methionine | — | — |
| Premix Nutrients | 0.15 | 0.15 |
| Crude protein, % | 15.44 | 15.78 |
| ME, kcal/kg | 3200 | 3200 |
| Crude fiber, % | 1.96 | 2.12 |
| Calcium, % | 0.85 | 0.85 |
| Phosphorus, % | 0.58 | 0.58 |
| Amino Acids, % | | |
| Arginine | 0.96 | 0.93 |
| Cysteine | 0.28 | 0.29 |
| Histidine | 0.40 | 0.42 |
| Isoleucine | 0.57 | 0.58 |
| Leucine | 1.39 | 1.49 |
| Lysine | 0.81 | 0.81 |
| Methionine | 0.26 | 0.34 |
| Phenylalanine | 0.70 | 0.72 |
| Threonine | 0.56 | 0.58 |
| Tryptophan | 0.14 | 0.14 |
| Tyrosine | 0.47 | 0.48 |
| Valine | 0.72 | 0.75 |

In Table 15, absolute values for ingredient percentages are given, however, in practice, the ingredients may include using the inclusion rates shown in other tables herein.

Some advantages of the new feed ration are that a user of the meal would not need to grind the corn, thus saving an energy intensive step, less soybean or other oilseed meal is required to meet desired protein levels, and the meal may have better digestibility than corn grain.

EXAMPLE 12

This example sets forth the use of the feed ration of this invention to fulfill the high-energy requirements of growing birds such as broilers. A poultry broiler finishing feed ration comprising an extracted corn meal containing less than or about 4% by weight oil (fat) is prepared by providing the following ingredients in the amounts indicated in the Table below. The feed ration is generally produced by blending, mixing, and pelleting the ingredients to produce a feed product; however, one or more of these steps can be omitted in the process of preparing the feed ration.

Table 16 shows the comparison of poultry feed rations made using normal corn (not solvent extracted) and extracted corn meal obtained from the current invention comprising about 12% by weight oil and about 9% by weight protein, wherein the extracted corn meal has about 4% by weight or less of oil (fat). Amounts are expressed on an "as is" or "as fed" moisture level and absolute values for ingredient percentages are given, however, in practice, the ingredients may be included using the inclusion rates shown in other tables herein.

TABLE 16

Growing Broilers

| Ingredients | Traditional Corn Feeds (%) | Extracted Corn Meal Blend (%) |
|---|---|---|
| Normal corn | 66.85 | — |
| Extracted corn meal (about 4% oil) | — | 70.86 |
| Soybean meal | 20.96 | 16.42 |
| Meat & bone meal | 5.00 | 5.00 |
| Feather meal | 2.00 | 2.00 |
| Fat | 3.29 | 3.76 |
| Salt | 0.37 | 0.37 |
| Added Lysine | 0.13 | 0.19 |
| Added Methionine | 0.15 | 0.09 |
| Premix | 0.10 | 0.10 |

TABLE 17

Growing Broilers

| Ingredients | Traditional Corn Feeds (%) | Extracted Corn Meal Blend (%) |
|---|---|---|
| Nutrients | | |
| Crude protein, % | 19.48 | 19.52 |
| ME, kcal/kg | 3100 | 3100 |
| Crude fiber, % | 1.97 | 2.12 |
| Calcium, % | 0.94 | 0.94 |
| Phosphorus, % | 0.63 | 0.62 |
| Amino Acids, % | | |
| Arginine | 1.27 | 1.23 |
| Cysteine | 0.38 | 0.39 |
| Histidine | 0.47 | 0.48 |
| Isoleucine | 0.78 | 0.79 |
| Leucine | 1.68 | 1.74 |
| Lysine | 1.06 | 1.06 |
| Methionine | 0.44 | 0.44 |
| Phenylalanine | 0.92 | 0.92 |
| Threonine | 0.74 | 0.75 |
| Tryptophan | 0.19 | 0.20 |
| Tyrosine | 0.61 | 0.62 |
| Valine | 0.95 | 0.96 |

The color of the crude oil is visually evaluated and determined to be a light yellow color compared to crude oil isolated using conventional wet milling methods, which is a dark brown color.

The desolventized corn meal is characterized using AOCS methods Ba 3-38, Ba 2b-82, Ba 6-84, and Ba 4e-93, and Corn Refiner's Method A-20. When normalized to 10% moisture content, the corn meal has about 3.2% by weight fiber content, about 65% by weight starch content, and about 14% by weight protein content. Meal fat is determined to be about 1.07% using AOCS method 3-38. For comparison, corn gluten feed created using conventional wet milling methods and normalized to a 10% moisture content can be expected to contain an oil content of about 4%, a protein content of about 20%, and a fiber and other carbohydrate content of about 60%, all by weight. Also for comparison, corn gluten meal created using conventional wet milling methods and normalized to a 10% moisture content can be expected to contain an oil content of about 3%, a protein content of about 60%, and a fiber and other carbohydrate content of about 22%, all by weight.

The nutrient profiles of meal (4.0% by weight oil) produced according to the process of the convention for use in the above blend are shown below in Table 18. Amounts are expressed on an "as is" or "as fed" moisture level.

TABLE 18

Meal Nutrient Profile

| Component | Meal Extracted (% by weight) |
|---|---|
| Moisture | 12 |
| Oil | 4 |
| Protein | 10.2 |
| Starch | 56.3 |
| Neutral Detergent Fiber | 11 |
| Acid Detergent Fiber | 2.8 |
| Ash | 1.3 |
| Lysine | 0.37 |
| Tryptophan | 0.102 |
| Methionine | 0.28 |
| Cystine | 0.24 |
| Total Sulfur Amino Acids | 0.52 |
| Valine | 0.51 |
| Isoleucine | 0.39 |
| Arginine | 0.51 |
| Threonine | 0.39 |
| Leucine | 1.17 |
| Histidine | 0.31 |
| Phenylalanine | 0.5 |
| Alanine | 0.79 |
| Serine | 0.52 |
| True metabolizable energy (TMEn; kcal/kg) | 3133 |
| Swine metabolizable energy (ME; kcal/kg) | 3301 |

The extracted corn meal prepared as described herein advantageously can be made to contain specific levels of oil and, in particular, specific ratios of oil to protein, of oil to carbohydrate or of oil to protein to carbohydrate. For example, normal yellow #2 corn with about 8% by weight protein and about 4% by weight oil has a protein to oil ratio of about 2.0, and high oil corn with about 9% by weight protein and about 12% by weight oil has a protein to oil ratio of about 0.75. Meal produced by extraction to have about 10% by weight protein and about 4% by weight oil has a protein to oil ratio of about 2.5. This higher ratio makes this meal type and products made from it desirable for certain applications, one example being a swine-finishing ration.

The present invention provides an extracted corn oil with greater amounts of beta-carotene than commercially available crude oil obtained from commodity normal yellow #2 corn. Conventional crude oil (i.e., oil produced from the corn wet milling process) can be obtained from suppliers such as Cargill, Incorporated (Minneapolis, Minn.). For example, a corn oil prepared as described above comprised the ingredients set forth in the Table 18 below in the amounts indicated as compared to commercially available crude oil.

TABLE 19

| Sample | Beta-Carotene (IU/100 g) |
|---|---|
| Commercial Crude Corn Oil | 15.5 |
| Oil Sample 1 | 152.1 |
| Oil Sample 2 | 159.1 |
| Oil Sample 3 | 158.1 |

EXAMPLE 13

This example details a comparison of two different feed rations: a first feed ration containing normal corn that has not been solvent extracted and a second feed ration containing extracted corn meal. The feed ration containing extracted corn meal is used when lean pork meat is a desired end product. The feed ration is generally produced by blending, mixing, and pelletting the ingredients to produce a feed product; however, one or more of these steps can be omitted in the process of preparing the feed ration. A hog finishing feed ration comprising an extracted corn meal containing less than or about 4% by weight oil is prepared by providing the following ingredients in the amounts set forth in Table 20. Table 20 also shows a comparison of swine feed rations made using normal corn (not high oil corn) and extracted corn meal obtained from high oil corn comprising about 12% by weight oil and about 9% by weight protein, wherein the extracted corn meal has about 1.5% by weight or less of oil (fat). Amounts are expressed on an "as is" or "as fed" moisture level.

TABLE 20

Swine Finishing Feeds

| Ingredients | Traditional Corn Feed (% by weight) | Extracted Corn Meal Blend (% by weight) |
|---|---|---|
| Corn | 79.98 | — |
| Extracted corn meal (about 4.0% by weight oil) | — | 81.05 |
| Soybean meal | 12.45 | 6.60 |
| Meat & bone meal | 6.59 | 7.22 |
| Feather meal | — | — |
| Fat | 0.10 | 4.0 |
| Salt | 0.40 | 0.70 |
| Lysine | 0.08 | 0.15 |
| Methionine | — | — |
| Premix | 0.15 | 0.15 |
| Nutrients | | |
| Crude protein, % | 15.44 | 15.38 |
| ME, kcal/kg | 3200 | 3200 |
| Crude fiber, % | 1.96 | 2.12 |
| Calcium, % | 0.85 | 0.85 |
| Phosphorus, % | 0.58 | 0.58 |
| Amino Acids, % | | |
| Arginine | 0.96 | 0.91 |
| Cysteine | 0.28 | 0.28 |
| Histidine | 0.40 | 0.41 |
| Isoleucine | 0.57 | 0.57 |
| Leucine | 1.39 | 1.45 |
| Lysine | 0.81 | 0.79 |
| Methionine | 0.26 | 0.33 |
| Phenylalanine | 0.70 | 0.70 |
| Threonine | 0.56 | 0.57 |
| Tryptophan | 0.14 | 0.13 |
| Tyrosine | 0.47 | 0.47 |
| Valine | 0.72 | 0.73 |

In Table 20, absolute values for ingredient percentages are given, however, in practice, the ingredients may include using the inclusion rates shown in other tables herein.

EXAMPLE 14

In this example, oil with approximately a 1.5 to 2 fold increase in tocotrienol content over conventionally produced crude corn oil is described. Using the method of cracking and extraction of Example 1, corn oil was extracted from high oil corn grain having an oil content of about 12% by weight. The corn oil was then analyzed for tocotrienol content. Table 21 includes data concerning the alpha- and gamma-tocotrienol content of conventional corn oils produced by conventional processing of conventional corn and the extracted corn oil prepared according to the method of Example 1.

Conventional crude oil refers to an unrefined corn oil sample produced by conventional wet milling methods. The sample is representative of corn oil of the type that is most commonly produced presently. As noted below, the tocotrienol content of extracted whole kernel oil (EWKO) samples from three different high oil corn samples that are extracted as described in Example 1 was found to be approximately 1.5 to 2 times higher than in the conventional crude oil sample. As shown in Table 21 below, the tocotrienol content of the EWKO samples range from about 6 ppm to about 8 ppm of α-tocotrienol and from about 18 ppm to about 21 ppm of γ-tocotrienol. Generally, increasing the extraction temperature resulted in an increase in the tocotrienol content of the extracted corn oil. The actual minimum and maximum values for tocotrienol content will depend upon the particular corn used.

TABLE 21

| | Tocotrienol Content | |
|---|---|---|
| Sample | α-tocotrienol (ppm) | γ-tocotrienol (ppm) |
| Conventional Crude Oil (Control) | 3.6 | 14.5 |
| EWKO 1 | 7.5 | 19.7 |
| EWKO 2 | 7.8 | 18.3 |
| EWKO 3 | 6.5 | 20.6 |

Accordingly, the process of Example 1 was used to make an extracted corn oil comprising elevated levels of tocotrienols.

EXAMPLE 15

This example illustrates a novel feed ingredient comprised of a blend of a corn meal produced by the cracking and oil extraction method and another plant-based meal such as an oilseed meal. This blended material can be in the form of simply a loose aggregate mixture of both meal types or a pelletted product. Because the method for producing the corn and oilseed meals is similar, i.e., cracking and solvent extraction, it is possible to produce both meals in proximity and blend them prior to shipment to a customer. An advantage of this approach is that varying protein and energy levels can be created in a single meal. Additional ingredients are optionally added either at the meal blending stage or at a later time. For example, an energy-intensive step in feed manufacturing involves grinding corn grain and blending it with other ingredients at a feed mill. The present blended meal generally requires less energy to produce a finished feed product than does a conventional blended meal.

Table 22 illustrates nutrient profiles of soybean meal (SBM), extracted corn meal (ECM), a blend of 20% SBM and 80% ECM (S20-C80), a blend of 10% SBM and 90% ECM (S10-C90), and nutrient requirements for poultry and swine diets. The poultry and swine nutrient requirements shown are in accordance with National Research Council (NRC) guidelines. The ECM is prepared according to Example 1.

TABLE 22

Feed Nutrient Profiles

| Parameter | SBM | ECM | 20% SBM & 80% ECM | Nutrient Needs for Poultry Diets | 10% SBM & 90% ECM | Nutrient Needs for Swine Diets |
|---|---|---|---|---|---|---|
| Crude Protein (CP) | 47.5 | 10.2 | 17.66 | 18 | 13.93 | 13.2 |
| Swine ME, kcal/kg | 3380 | 3301 | 3316.8 | | 3308.90 | 3265 |
| Poultry ME, kcal/kg | 2440 | 3133 | 2994.4 | 3200 | 3063.70 | |
| Crude Fat, % | 3 | 4 | 3.8 | | 3.90 | |
| Neutral Detergent Fiber, % | 8.9 | 11.3 | 10.82 | | 11.06 | |
| Acid Detergent Fiber, % | 5.4 | 2.8 | 3.32 | | 3.06 | |
| Arginine | 3.48 | 0.45 | 1.06 | 1.00 | 0.75 | 0.19 |
| Histidine | 1.28 | 0.27 | 0.47 | 0.27 | 0.37 | 0.19 |
| Isoleucine | 2.16 | 0.34 | 0.70 | 0.62 | 0.52 | 0.33 |
| Leucine | 3.66 | 1.03 | 1.56 | 0.93 | 1.29 | 0.54 |
| Lysine | 3.02 | 0.33 | 0.87 | 0.85 | 0.60 | 0.60 |
| Methionine | 0.67 | 0.25 | 0.33 | 0.32 | 0.29 | 0.16 |
| Cysteine | 0.74 | 0.21 | 0.32 | 0.28 | 0.26 | 0.35 |
| Phenylalanine | 2.39 | 0.44 | 0.83 | 0.56 | 0.64 | 0.34 |
| Tyrosine | 1.82 | 0.29 | 0.60 | 0.48 | 0.44 | 0.55 |
| Threonine | 1.85 | 0.34 | 0.64 | 0.68 | 0.49 | 0.41 |
| Tryptophan | 0.65 | 0.09 | 0.20 | 0.16 | 0.15 | 0.11 |
| Valine | 2.27 | 0.45 | 0.81 | 0.70 | 0.63 | 0.40 |
| Total Essential Amino Acids (EAA) | 23.99 | 4.49 | 8.39 | 6.85 | 6.44 | 4.17 |
| EAA/CP | 0.505 | 0.440 | 0.45 | 0.381 | 0.45 | 0.316 |

This example sets forth a description of using the extracted corn meal of the present invention to produce biodegradable materials with improved tensile strength. Corn meal of the present invention is suspended in hexanes in a sealed container, at a 2:3 corn meal: solvent weight ratio. The mixture is allowed to stand at room temperature without mixing for about 18 hours. The organic solvent is removed from the extracted corn meal, and the extracted corn meal residue is washed during filtering with an aliquot of hexanes in a 1:1 residue: solvent weight ratio. The residue is dried in a convection oven at 50° C. for 16 hours. The dried residue is sprayed with water with mixing until the moisture content of the residue is 10.7% to 11.3%. The solvent-treated extracted corn meal composition is molded into an ASTM standard dogbone article using a compression molding press (Wabash Metal Products, Inc. Wabash, Ind.) at 5000 psi, 140° C. to 160° C. for 10 minutes. The untreated corn meal composition is likewise combined with water to about 10.7% to 11.3% water content and molded into an ASTM standard dogbone article. The articles produced with the solvent-treated extracted corn meal will exhibit significantly improved tensile properties as compared to non-solvent treated extracted corn meal.

Alternatively, corn meal of the present invention is separately suspended in aqueous ethanol (95%) at a 1:3 weight-ratio of meal to oil, and boiled for 2 hours with reflux and mechanical stirring. The meal is filtered and the residues are washed with ethanol (1:1 residue: ethanol). The residues are dried, remoistened, and molded according to the procedure above. Tensile properties and water-absorption of the meal treated with ethanol at boiling temperature for a short 2 hour period would be similar to the meals treated at room temperature for an extended 18 hour period.

EXAMPLE 17

This example sets forth the use of meal derived from corn processed through cracking and extraction as a component of a hog finishing feed ration. This example details a comparison of two different feed rations: a first feed ration containing normal corn that has not been solvent extracted and a second feed ration containing extracted corn meal. The feed ration containing extracted corn meal is used when lean pork meat is a desired end product. Table 23 presents a comparison of swine feed rations made using normal corn (not solvent extracted) and extracted corn meal obtained from the current invention comprising about 6.0% by weight or less of oil (fat). The feed ration is generally produced by blending, mixing, and pelleting the ingredients to produce a feed product; however, one or more of these steps can be omitted in the process of preparing the feed ration. Amounts are expressed on an "as is" or "as fed" moisture level.

TABLE 23

Swine Grower Feeds

| Ingredients | Traditional Corn Feed (%) | Extracted Corn Meal Blend (%) |
|---|---|---|
| Corn | 45.56 | — |
| Extracted corn meal (about 6.0% by weight oil) | — | 46.77 |
| Wheat middlings | 20.00 | 20.00 |
| Meat & bone meal | 2.29 | 2.39 |
| Hydrolyzed Feathermeal | — | — |
| Soybean meal | 14.77 | 14.17 |
| Tallow | 2.99 | 2.72 |
| Bakery | 10.00 | 10.00 |
| Fat | 6.97 | 7.60 |
| Salt | 0.3 | 0.95 |
| Crude Protein, % | 18.28 | 18.53 |

TABLE 23-continued

Swine Grower Feeds

| Ingredients | Traditional Corn Feed (%) | Extracted Corn Meal Blend (%) |
|---|---|---|
| Nutrients | | |
| Calcium, % | 0.8 | 0.8 |
| Phosphorus, % | 0.70 | 0.70 |
| ME, kcal/kg | 2140.0 | 2140.0 |
| Amino Acids, % | | |
| Arginine | 1.12 | 1.12 |
| Cysteine | 0.37 | 0.36 |
| Glycine | 0.98 | 0.87 |
| Histidine | 0.42 | 0.45 |
| Isoleucine | 0.69 | 0.70 |
| Leucine | 1.47 | 1.56 |
| Lysine | 1.11 | 1.11 |
| Methionine | 0.32 | 0.32 |
| Phenylalanine | 0.82 | 0.84 |
| Serine | 0.0 | 0.0 |
| Threonine | 0.74 | 0.74 |
| Tryptophan | 0.19 | 0.19 |
| Tyrosine | 0.51 | 0.54 |
| Valine | 0.86 | 0.86 |
| Methionine/Cystine | 0.69 | 0.67 |

In Table 23, absolute values for ingredient percentages are given, however, in practice, the ingredients may include using the inclusion rates shown in other tables herein.

Some advantages of the new feed ration are that a user of the meal would not need to grind the corn, thus saving an energy intensive step, less soybean or other oilseed meal is required to meet desired protein levels, and the meal may have better digestibility than corn grain.

The nutrient profiles of meal (6.0% by weight oil) produced according to the present invention for use in the extracted corn meal blend set forth in Table 23 are shown in Table 24 below. Amounts are expressed on an "as is" or "as fed" moisture level.

TABLE 24

Extracted Corn Meal Nutrient Profile

| Component | Extracted Meal (% by weight) |
|---|---|
| Moisture | 14.0 |
| Oil | 6.0 |
| Protein | 10.2 |
| Starch | 67 |
| Neutral Detergent Fiber | 7.3 |
| Acid Detergent Fiber | 1.6 |
| Ash | 1.4 |
| Lysine | 0.29 |
| Tryptophan | 0.07 |
| Methionine | 0.20 |
| Cystine | 0.22 |
| Valine | 0.48 |
| Isoleucine | 0.36 |
| Arginine | 0.45 |
| Threonine | 0.36 |
| Leucine | 1.31 |
| Histidine | 0.2 |
| Phenylalanine | 0.49 |
| Serine | 0 |
| True metabolizable energy (TMEn; kcal/kg) | 2290 |
| Swine metabolizable energy (ME; kcal/kg) | 3383 |

EXAMPLE 18

This example sets forth the use of the feed ration of this invention to fulfill the high-energy requirements of growing birds such as broilers. A poultry broiler finishing feed ration comprising an extracted corn meal containing less than or about 6% by weight oil (fat) is prepared by providing the following ingredients in the amounts indicated in the Table below. The feed ration is generally produced by blending, mixing, and pelleting the ingredients to produce a feed product; however, one or more of these steps can be omitted in the process of preparing the feed ration.

Table 25 presents a comparison of poultry feed rations made using normal corn (not solvent extracted) and extracted corn meal obtained from the current invention comprising about 12.5% by weight oil, and about 10% by weight protein, wherein the extracted corn meal has about 6% by weight or less of oil (fat). Amounts are expressed on an "as is" or "as fed" moisture level and absolute values for ingredient percentages are given, however, in practice, the ingredients may be included using the inclusion rates shown in other tables herein.

TABLE 25

Growing Broiler/Feeds

| Ingredients | Traditional Corn Feed (%) | Extracted Corn Meal Blend (%) |
|---|---|---|
| Yellow #2 Corn | 49.78 | — |
| Extracted corn meal (about 6% oil) | — | 59.72 |
| Wheat Middlings | 10.0 | 1.11 |
| Meat & bone meal | 6.43 | 0.00 |
| Hydrolyzed Feathermeal | 3.00 | 2.74 |
| Soybean Meal | 15.70 | 19.65 |
| Fat | 7.94 | 8.0 |
| Tallow | 3.91 | 3.04 |
| Bakery | 10.00 | 10.00 |
| Nutrients | | |
| Crude Protein, % | 20.19 | 19.25 |
| Fiber, % | 2.47 | 1.80 |
| Calcium, % | 0.94 | 0.94 |
| Energy, kcal/kg | 3150.0 | 3150.0 |
| Amino Acids, % | | |
| Arginine | 1.29 | 1.17 |
| Cysteine | 0.42 | 0.41 |
| Glycine | 1.24 | 0.82 |
| Histidine | 0.46 | 0.46 |
| Isoleucine | 0.78 | 0.80 |
| Leucine | 1.63 | 1.79 |
| Lysine | 1.07 | 1.05 |
| Methionine | 0.43 | 0.43 |
| Phenylalanine | 0.91 | 0.94 |
| Serine | 0.0 | 0.0 |
| Threonine | 0.74 | 0.73 |
| Tryptophan | 0.20 | 0.19 |
| Tyrosine | 0.60 | 0.60 |
| Valine | 0.98 | 0.95 |
| Met/Cys | 0.86 | 0.84 |

The color of the crude oil is visually evaluated and determined to be a light yellow color compared to crude oil isolated using conventional wet milling methods, which is a dark brown color.

The desolventized corn meal is characterized using AOCS methods Ba 3-38, Ba 2b-82, Ba 6-84, and Ba 4e-93, and Corn Refiner's Method A-20. When normalized to 14% moisture content, the corn meal has about 1.8% fiber content, about 67% starch content, and about 10.15% protein content. Meal fat is determined to be about 6% using AOCS method 3–38. For comparison, corn gluten feed created using conventional wet milling methods and normalized to a 10% moisture content can be expected to contain an oil content of about 4%, a protein content of about 20%, and a fiber and other carbohydrate content of about 60%. Also for comparison, corn gluten meal created using conventional wet milling methods and normalized to a 10% moisture content can be expected to contain an oil content of about 3%, a protein content of about 60%, and a fiber and other carbohydrate content of about 22%.

The nutrient profiles of meal (6.0% by weight oil) produced according to the present invention for use in the extracted corn meal blend set forth in Table 25 are shown in Table 26 below. Amounts are expressed on an "as is" or "as fed" moisture level.

TABLE 26

Extracted Corn Meal Nutrient Profile

| Component | Extracted Meal (% by weight) |
|---|---|
| Moisture | 14 |
| Oil | 6.0 |
| Protein | 10.15 |
| Starch | 67 |
| Neutral Detergent Fiber | 7.29 |
| Acid Detergent Fiber | 1.59 |
| Ash | 1.37 |
| Lysine | 0.29 |
| Tryptophan | 0.07 |
| Methionine | 0.20 |
| Cystine | 0.22 |
| Total Sulfur Amino Acids | 0.52 |
| Valine | 0.48 |
| Isoleucine | 0.36 |
| Arginine | 0.45 |
| Threonine | 0.36 |
| Leucine | 1.31 |
| Histidine | 0.28 |
| Phenylalanine | 0.49 |
| Serine | 0 |
| True metabolizable energy (TMEn; kcal/kg) | 2290 |
| Swine metabolizable energy (ME; kcal/kg) | 3383 |

When compared to meals made from normal yellow #2 corn, the extracted corn meal described herein provides a greater amount of key nutritional components such as vitamin $B_6$. For example, the meal sample in Table 25 includes the vitamin $B_6$ components in the amount shown in Table 27 below. The amount for the same component, to the extent they are found in yellow corn that has not been processed as described herein, are included for comparison.

TABLE 27

Vitamin $B_6$ Content

| Component | Yellow Corn | Meal Sample |
|---|---|---|
| Vitamin $B_6$ (mg/100 g) | 0.400 | 0.660 |

The extracted corn meal prepared as described herein advantageously can be made to contain specific levels of oil and, in particular, specific ratios of oil to protein, of oil to carbohydrate or of oil to protein to carbohydrate. For example, normal corn with about 8% by weight protein and about 4% by weight oil has a protein: oil ratio of about 2.0, and high oil corn with about 9% by weight protein and about 12% by weight oil has a protein: oil ratio of about 0.75. Meal produced by extraction to have about 10% by weight protein and about 6% by weight oil has a protein: oil ratio of about 1.67. This higher ratio makes this meal type and products made from it desirable for certain applications, one example being a swine-finishing ration.

The present invention provides an extracted corn oil with greater amounts of beta-carotene than commercially available crude oil obtained from commodity normal yellow #2 corn. Conventional crude oil can be obtained from suppliers such as Cargill, Incorporated (Minneapolis, Minn.). For example, a corn oil prepared as described above in Example 1 by extraction comprises the ingredients shown in Table 28 in the amounts indicated as compared to commercially available crude oil.

TABLE 28

Beta Carotene Content

| Sample | Beta-Carotene (IU/100 g) |
|---|---|
| Commercial Crude Corn Oil | 15.5 |
| SEC Oil Sample 1 | 152.1 |
| SEC Oil Sample 2 | 159.1 |
| SEC Oil Sample 3 | 158.1 |

EXAMPLE 19

This example details a comparison of two different feed rations: a first feed ration containing normal corn that has not been solvent extracted and a second feed ration containing extracted corn meal. The feed ration containing extracted corn meal is used when lean beef meat is a desired end product. A beef cattle/dairy finishing feed ration comprising an extracted corn meal containing less than or about 6% by weight oil is prepared by providing the following ingredients in the amounts indicated in Table 25. The feed ration is generally produced by blending, mixing, and pelleting the ingredients to produce a feed product; however, one or more of these steps can be omitted in the process of preparing the feed ration. Table 29 shows a comparison of beef cattle/dairy feed rations made using yellow #2 corn and extracted corn meal obtained from high oil corn comprising 12.5% by weight oil, 10% by weight protein, wherein the extracted corn meal has about 6.0% by weight or less of oil (fat). Amounts are expressed on an "as is" or "as fed" moisture level.

TABLE 29

Dairy Finishing Feeds

| Ingredients | Normal Corn Feed (% by weight) | Extracted Corn Meal Blend (% by weight) |
|---|---|---|
| Corn | 29.44 | 16.03 |
| Extracted corn meal (about 6.0% by weight oil) | — | 14.93 |
| Wheat Middlings | 30.0 | 30.0 |
| Meat & bone meal | 0.00 | 0.00 |
| Hydrolyzed Feathermeal | 2.03 | 2.24 |
| Soybean Meal | 10.46 | 10.27 |
| Tallow | 0.51 | 0.08 |
| Fat | 4.0 | 4.0 |
| Bakery | 10.00 | 10.00 |
| Corn Gluten Feed | 6.02 | 5.35 |

TABLE 29-continued

Dairy Finishing Feeds

| Ingredients | Normal Corn Feed (% by weight) | Extracted Corn Meal Blend (% by weight) |
|---|---|---|
| Nutrients | | |
| Crude Protein | 20.0 | 20.0 |
| Neutral Detergent Fiber | 16.51 | 16.47 |
| Acid Detergent Fiber | 6.83 | 6.78 |
| Fiber | 5.65 | 5.59 |
| Dry Matter | 88.56 | 55.40 |
| Salt | 1.0 | 1.0 |
| Calcium | 1.2 | 1.2 |
| Phosphorus | 0.53 | 0.53 |
| Potassium | 0.80 | 0.80 |
| Magnesium | 0.23 | 0.23 |
| Sulfur | 0.21 | 0.21 |
| Sodium | 0.48 | 0.50 |
| Chlor | 0.57 | 0.58 |
| Net Energy of Lactation, MCAL/CWT | 75.88 | 75.54 |
| Net Energy of Gain KG, MCAL/KG | 1.10 | 1.10 |
| Net Energy of Lactation MJ, MJ/KG | 6.99 | 6.96 |

TABLE 30

Dairy Finishing Needs

| Ingredients | Normal Corn Feed (% by weight) | Extracted Corn Meal Blend (% by weight) |
|---|---|---|
| Amino Acids, % | | |
| Arginine | 1.15 | 1.15 |
| Cysteine | 0.44 | 0.45 |
| Glycine | 0.88 | 0.87 |
| Histidine | 0.47 | 0.47 |
| Isoleucine | 0.80 | 0.80 |
| Leucine | 1.90 | 1.89 |
| Lysine | 0.76 | 0.76 |
| Methionine | 0.33 | 0.33 |
| Phenylalanine | 0.99 | 0.98 |
| Serine | 0.003 | 0 |
| Threonine | 0.72 | 0.72 |
| Tryptophan | 0.22 | 0.21 |
| Tyrosine | 0.67 | 0.66 |
| Valium | 0.97 | 0.98 |
| Met/Cys | 0.73 | 0.73 |

In Table 30, absolute values for ingredient percentages are given, however, in practice, the ingredients may include using the inclusion rates shown in other tables herein.

The nutrient profiles of meal (6.0% by weight oil) produced according to the present invention for use in the extracted corn meal blend set forth in Table 30 are shown in Table 31 below. Amounts are expressed on an "as is" or "as fed" moisture level.

TABLE 31

Extracted Corn Meal Nutrient Profile

| Component | Extracted Meal (% by weight) |
|---|---|
| Moisture | 14.0 |
| Oil | 6.0 |
| Protein | 10.2 |
| Starch | 67 |

TABLE 31-continued

Extracted Corn Meal Nutrient Profile

| Component | Extracted Meal (% by weight) |
|---|---|
| Neutral Detergent Fiber | 7.3 |
| Acid Detergent Fiber | 1.6 |
| Ash | 1.4 |
| Lysine | 0.29 |
| Tryptophan | 0.07 |
| Methionine | 0.20 |
| Cysteine | 0.22 |
| Valine | 0.48 |
| Isoleucine | 0.36 |
| Arginine | 0.45 |
| Threonine | 0.36 |
| Leucine | 1.31 |
| Histidine | 0.28 |
| Phenylalanine | 0.49 |
| Serine | 0 |
| True metabolizable energy (TMEn; kcal/kg) | 2290 |
| Swine metabolizable energy (ME; kcal/kg) | 3383 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon the foregoing description. The inventors expect skilled artisans to employ such variations as appropriate, and the inventors intend the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for producing fermentation-based products comprising:
   (a) combining an enzyme, water, and a corn meal obtained by cracking the corn, conditioning the corn, and extracting the corn to produce corn meal and corn oil, wherein the corn is not flaked during processing;
   (b) incubating the combination; and
   (c) mixing the combination with a micro-organism capable of fermenting a carbon source to produce a fermentation-based product.

2. The method of claim 1, further comprising the step of tempering the corn.

3. The method of claim 2, wherein the step of conditioning is after the step of tempering the corn.

4. The method of claim 3, wherein the step of cracking is after the step of tempering and before the step of conditioning the corn.

5. The method of claim 1 wherein the enzyme is selected from the group consisting of an amylase, a protease, a cellulase, an esterase and a liginase.

6. The method of claim 5, wherein the enzyme is an amylase.

7. The method of claim 6, wherein the enzyme is glucoamylase.

8. The method of claim 5, wherein the enzyme is a cellulase.

9. The method of claim 8, wherein the cellulase is xylonase.

10. The method of claim 5, wherein the enzyme is an esterase.

11. The method of claim 10, wherein the esterase is selected from the group consisting of ferulase and acetylesterase.

12. The method of claim 5, wherein the enzyme is a protease.

13. The method of claim 5, wherein the enzyme is a liginase.

14. The method of claim 1, wherein the oil content of the whole corn is from about 3% by weight to about 30% by weight.

15. The method of claim 1, wherein the oil content is from about 6% by weight to about 12% by weight.

16. The method of claim 1, wherein the fermentation-based product is ethanol.

17. The method of claim 1, wherein the fermentation based product is citric acid.

* * * * *